United States Patent
Nicholas

(10) Patent No.: US 11,617,581 B2
(45) Date of Patent: Apr. 4, 2023

(54) TOOL ASSEMBLY WITH MINIMAL DEAD SPACE

(71) Applicant: Covidien LP, Mansfield, MA (US)

(72) Inventor: David Nicholas, Trumbull, CT (US)

(73) Assignee: Covidien LP, Mansfield, MA (US)

(*) Notice: Subject to any disclaimer, the term of this patent is extended or adjusted under 35 U.S.C. 154(b) by 266 days.

(21) Appl. No.: 16/686,778

(22) Filed: Nov. 18, 2019

(65) Prior Publication Data

US 2020/0085432 A1 Mar. 19, 2020

Related U.S. Application Data

(63) Continuation of application No. 15/612,176, filed on Jun. 2, 2017, now Pat. No. 10,478,185.

(51) Int. Cl.
*A61B 17/072* (2006.01)
*A61B 1/00* (2006.01)
(Continued)

(52) U.S. Cl.
CPC .... *A61B 17/07207* (2013.01); *A61B 1/00087* (2013.01); *A61B 17/068* (2013.01);
(Continued)

(58) Field of Classification Search
CPC .......... A61B 17/07207; A61B 1/00087; A61B 17/068; A61B 2017/00353;
(Continued)

(56) References Cited

U.S. PATENT DOCUMENTS

| 3,079,606 A | 3/1963 | Bobrov et al. |
| 3,490,675 A | 1/1970 | Green et al. |

(Continued)

FOREIGN PATENT DOCUMENTS

| AU | 198654765 | 9/1986 |
| AU | 2014259548 A1 * | 8/2015 |

(Continued)

OTHER PUBLICATIONS

Partial European Search Report dated Nov. 23, 2018, issued in EP Appln. No. 18175519.

(Continued)

*Primary Examiner* — Robert F Long
(74) *Attorney, Agent, or Firm* — Carter, DeLuca & Farrell LLP

(57) ABSTRACT

A surgical stapling device includes a handle assembly, an elongate body extending distally from the handle assembly, and a tool assembly. The tool assembly includes an actuation sled that is movable through a staple cartridge to eject staples from the staple cartridge and a clamp member that is movable through the tool assembly to move the tool assembly from an open position to an approximated position. In order to minimize dead space in a proximal portion of the tool assembly, the actuation sled and clamp member are supported in a nested relationship in a pre-actuated state of the surgical stapling device. The clamp member is subsequently moved to a position proximal of the actuation sled during a firing stroke of the stapling device.

18 Claims, 17 Drawing Sheets

(51) Int. Cl.
  *A61B 17/00* (2006.01)
  *A61B 17/068* (2006.01)
  *A61B 17/29* (2006.01)

(52) U.S. Cl.
  CPC ............ *A61B 2017/00353* (2013.01); *A61B 2017/00398* (2013.01); *A61B 2017/00734* (2013.01); *A61B 2017/07278* (2013.01); *A61B 2017/07285* (2013.01); *A61B 2017/2927* (2013.01)

(58) Field of Classification Search
  CPC ........... A61B 2017/00398; A61B 2017/00734; A61B 2017/07278; A61B 2017/07285; A61B 2017/2927; A61B 17/00234; A61B 2017/07271
  USPC .......................................... 227/175.1–182.1
  See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Ley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |

(56) References Cited

U.S. PATENT DOCUMENTS

| | | |
|---|---|---|
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Ley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A * | 1/2000 | Johnson ........... A61B 17/07207 227/176.1 |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |

(56) References Cited

U.S. PATENT DOCUMENTS

| | | |
|---|---|---|
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |

(56) References Cited

U.S. PATENT DOCUMENTS

| | | |
|---|---|---|
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |

(56) References Cited

U.S. PATENT DOCUMENTS

| | | |
|---|---|---|
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 3,002,795 A1 | 8/2011 | Beetel |
| 3,006,885 A1 | 8/2011 | Marczyk |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, Iv et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |

(56) References Cited

U.S. PATENT DOCUMENTS

| | | |
|---|---|---|
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |

(56) References Cited

U.S. PATENT DOCUMENTS

| | | |
|---|---|---|
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 3,820,603 A1 | 9/2014 | Shelton, IV et al. |
| 3,820,605 A1 | 9/2014 | Shelton, IV |
| 3,820,607 A1 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 * | 8/2015 | Morgan ............... A61B 17/068 |
| 9,113,870 B2 | 8/2015 | Viola |
| 9,113,872 B2 | 8/2015 | Viola |

(56) References Cited

U.S. PATENT DOCUMENTS

| | | |
|---|---|---|
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,138,226 B2 * | 9/2015 | Racenet ............ A61B 17/07207 |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Mdridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,808,248 B2 * | 11/2017 | Hoffman ............ A61B 17/07207 |
| 10,478,185 B2 | 11/2019 | Nicholas |
| 10,517,591 B2 * | 12/2019 | Olson ................. A61B 17/068 |
| 10,537,324 B2 * | 1/2020 | Shelton, IV ......... A61B 17/072 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0023324 A1 | 2/2005 | Doll et al. |
| 2005/0216055 A1 | 9/2005 | Scirica et al. |
| 2006/0011699 A1 * | 1/2006 | Olson ............... A61B 17/07207 227/180.1 |
| 2006/0016853 A1 * | 1/2006 | Racenet ............ A61B 17/07207 227/176.1 |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0006620 A1 | 1/2010 | Sorrentino et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087259 A1 * | 4/2011 | Marczyk ............ A61B 17/072 606/170 |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |

(56) References Cited

U.S. PATENT DOCUMENTS

| | | |
|---|---|---|
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0274722 A1* | 10/2013 | Kostrzewski ......... A61B 17/29 606/1 |
| 2013/0277410 A1 | 10/2013 | Fernandez et al. |
| 2013/0313305 A1* | 11/2013 | Scirica ............ A61B 17/07207 227/180.1 |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0284372 A1 | 9/2014 | Kostrzewski |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1* | 6/2015 | Shelton, IV ........... A61B 34/37 227/176.1 |
| 2015/0173750 A1 | 6/2015 | Shelton, IV et al. |

(56) References Cited

U.S. PATENT DOCUMENTS

| | | |
|---|---|---|
| 2015/0173751 A1 | 6/2015 | Shelton, IV |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0324317 A1* | 11/2015 | Collins .............. G06F 13/4221 710/106 |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0303926 A1* | 10/2017 | Scheib ............. A61B 17/07207 |
| 2018/0125485 A1 | 5/2018 | Beardsley et al. |
| 2018/0168628 A1 | 6/2018 | Hunter |
| 2018/0344318 A1* | 12/2018 | Nicholas ............ A61B 1/00087 |
| 2019/0125342 A1 | 5/2019 | Beardsley |

FOREIGN PATENT DOCUMENTS

| | | |
|---|---|---|
| CA | 2773414 A1 | 11/2012 |
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| EP | 3318199 A1 | 5/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |

(56) References Cited

FOREIGN PATENT DOCUMENTS

| | | |
|---|---|---|
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2004344659 A | 12/2004 |
| JP | 2017500147 A | 1/2017 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |
| WO | 2014175894 A1 | 10/2014 |
| WO | 20150191887 A1 | 12/2015 |

OTHER PUBLICATIONS

European Search Report dated Mar. 4, 2019, issued in EP Appln. No. 18175519.
Japanese Office Action dated Apr. 18, 2022, issued in corresponding JP Appln. No. 2018-099654, 5 pages.
Chinese Office Action dated Aug. 29, 2022, issued in corresponding CN Application No. 201810558974, 8 pages.

\* cited by examiner

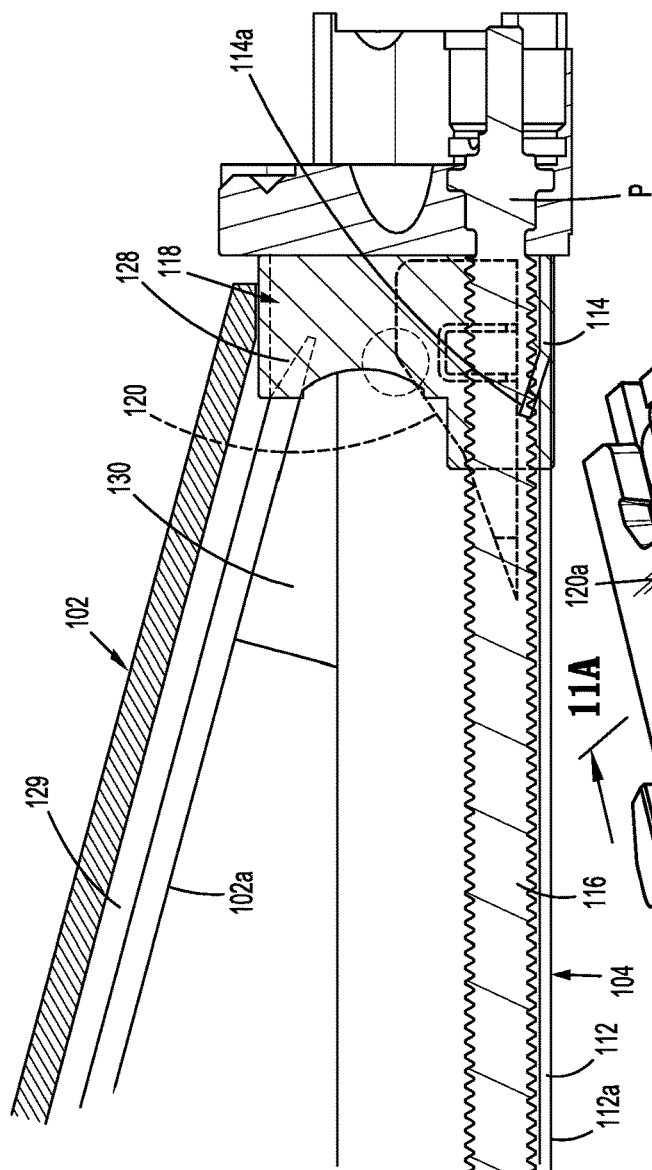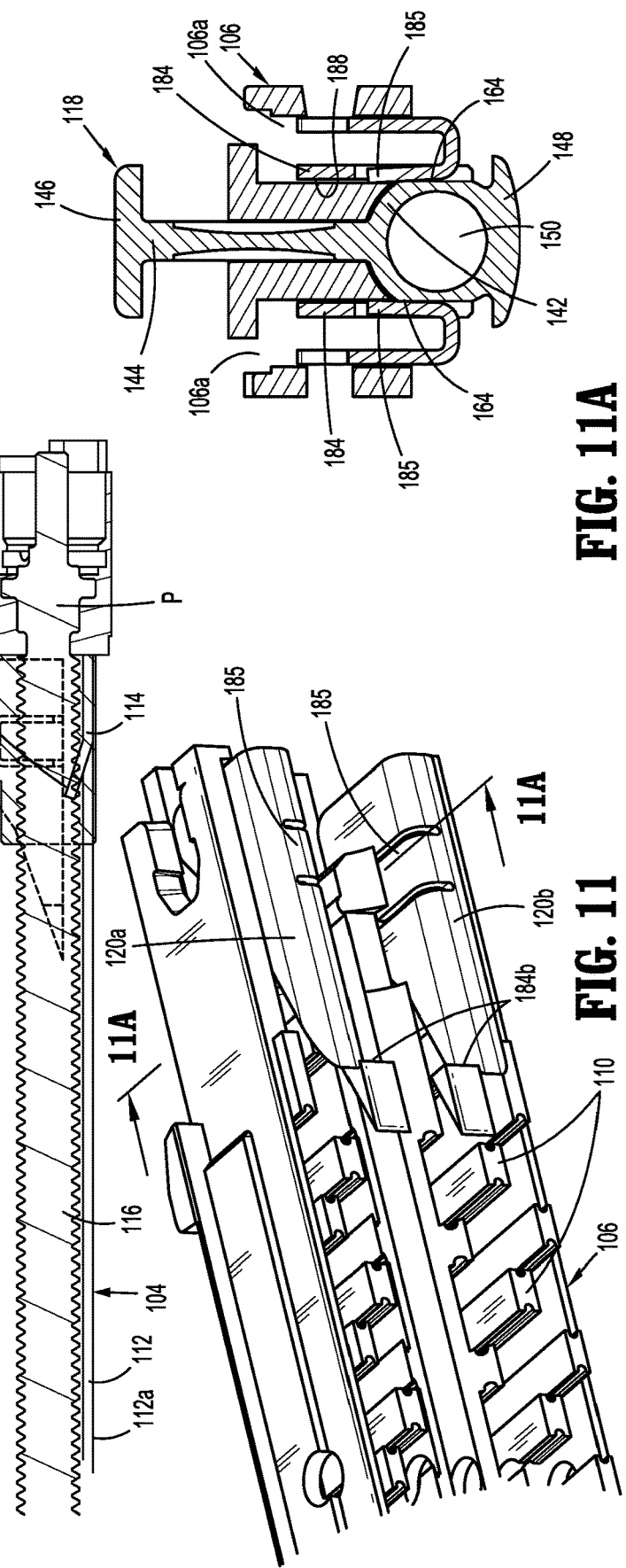

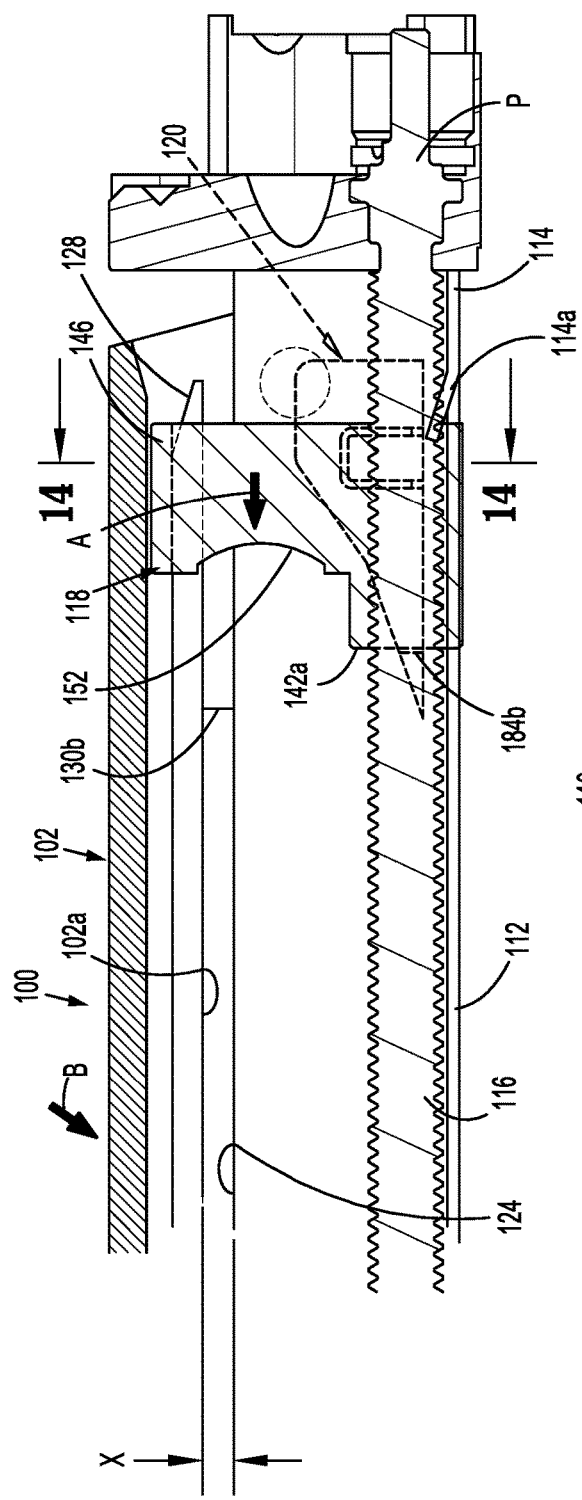
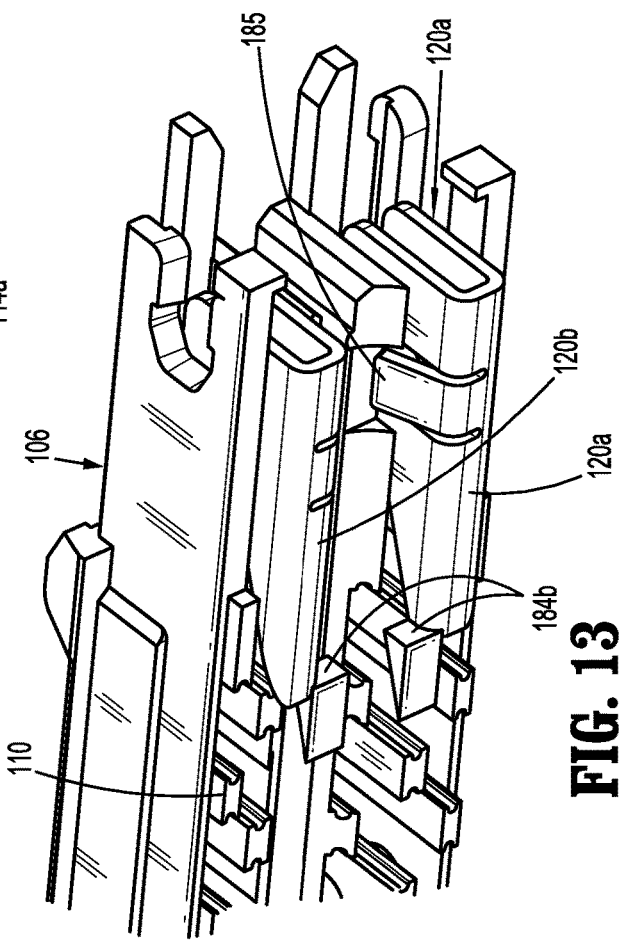

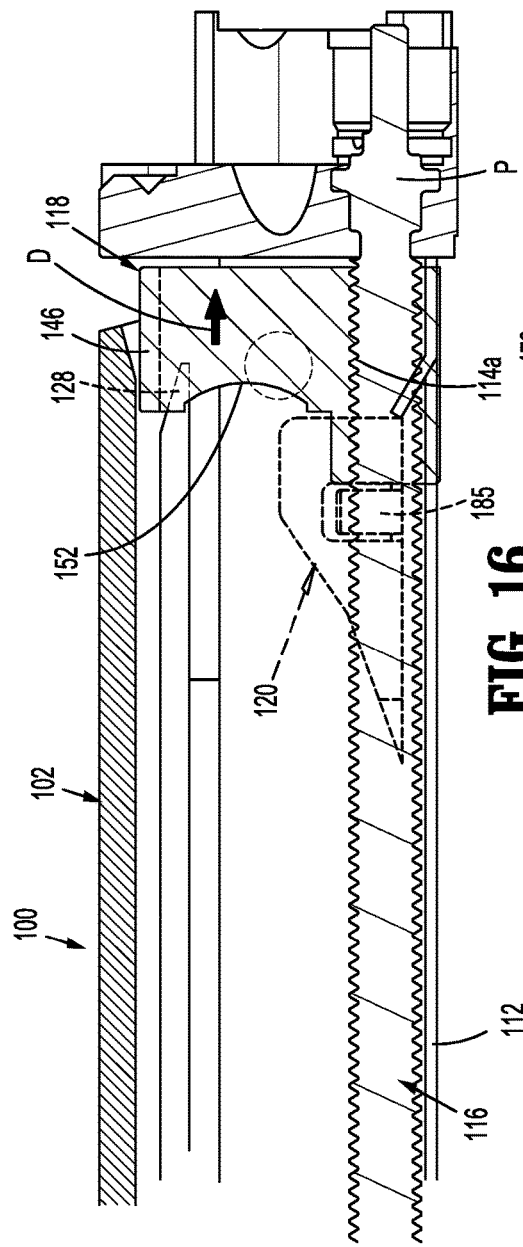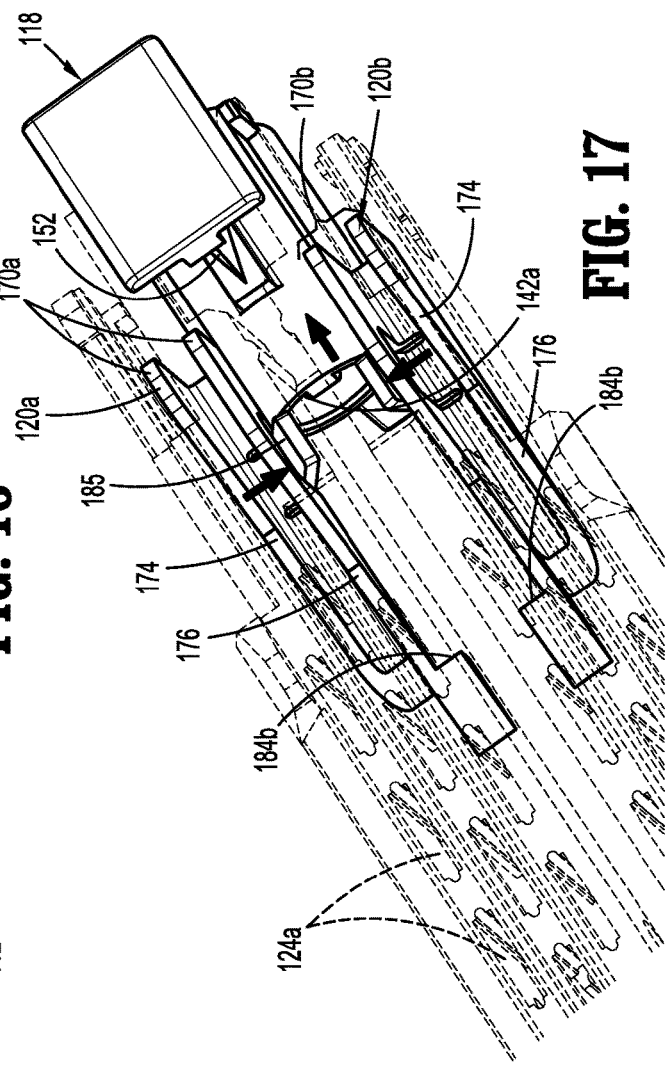

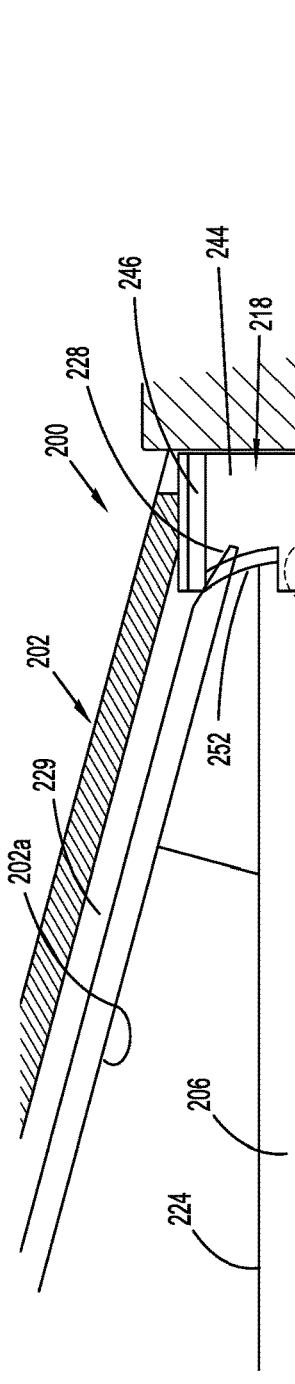
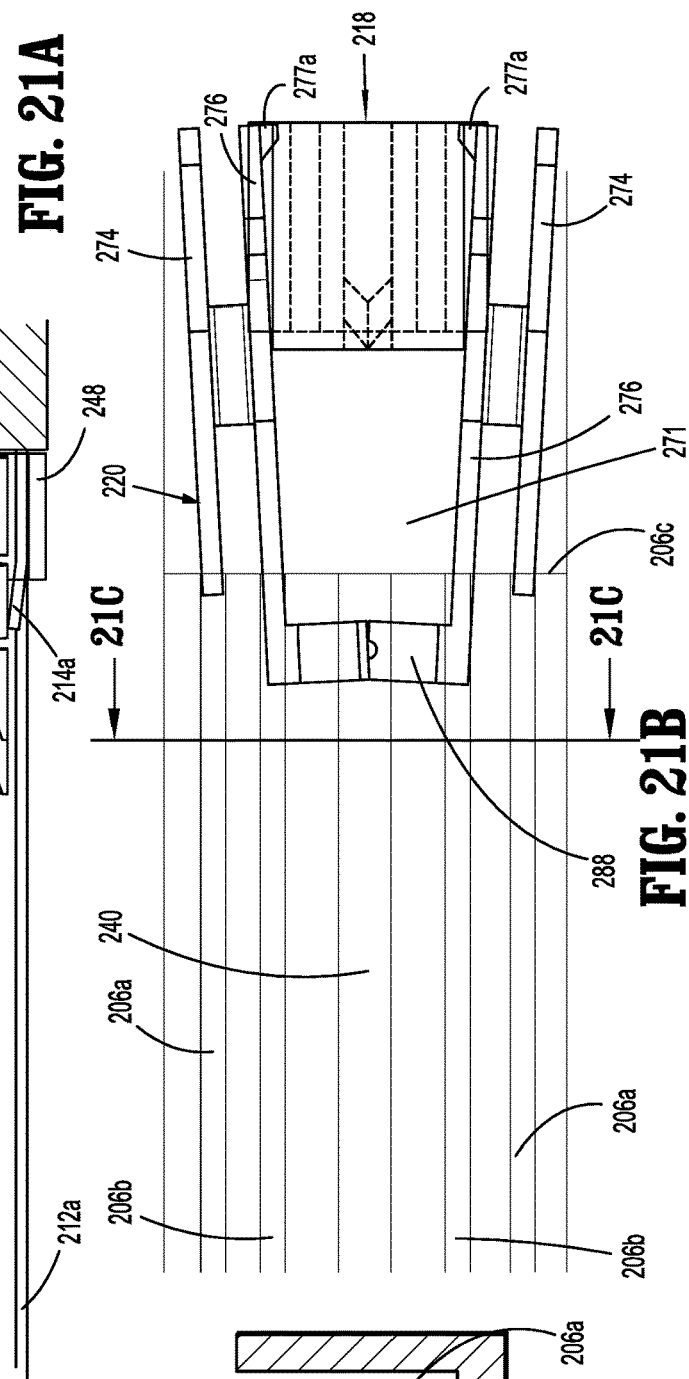
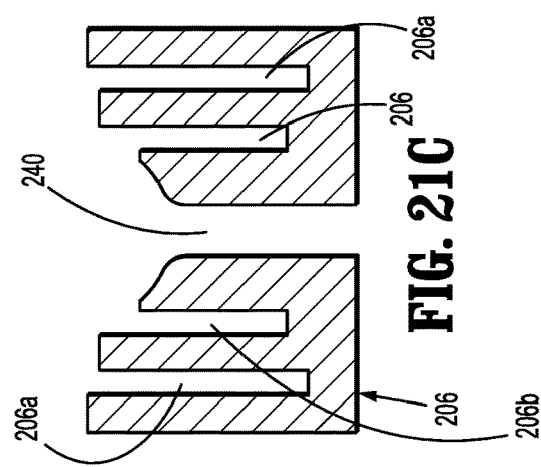
FIG. 21A
FIG. 21B
FIG. 21C

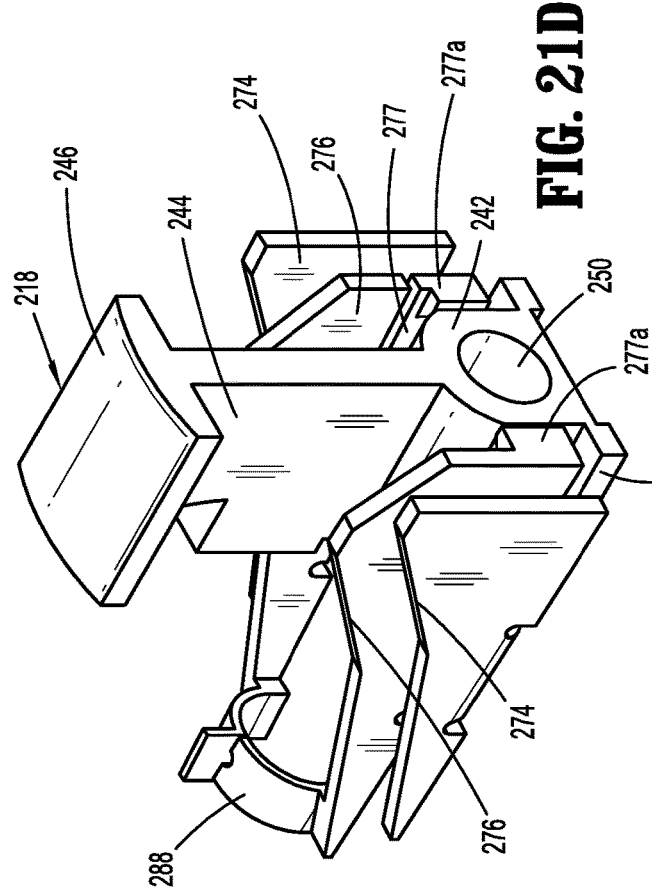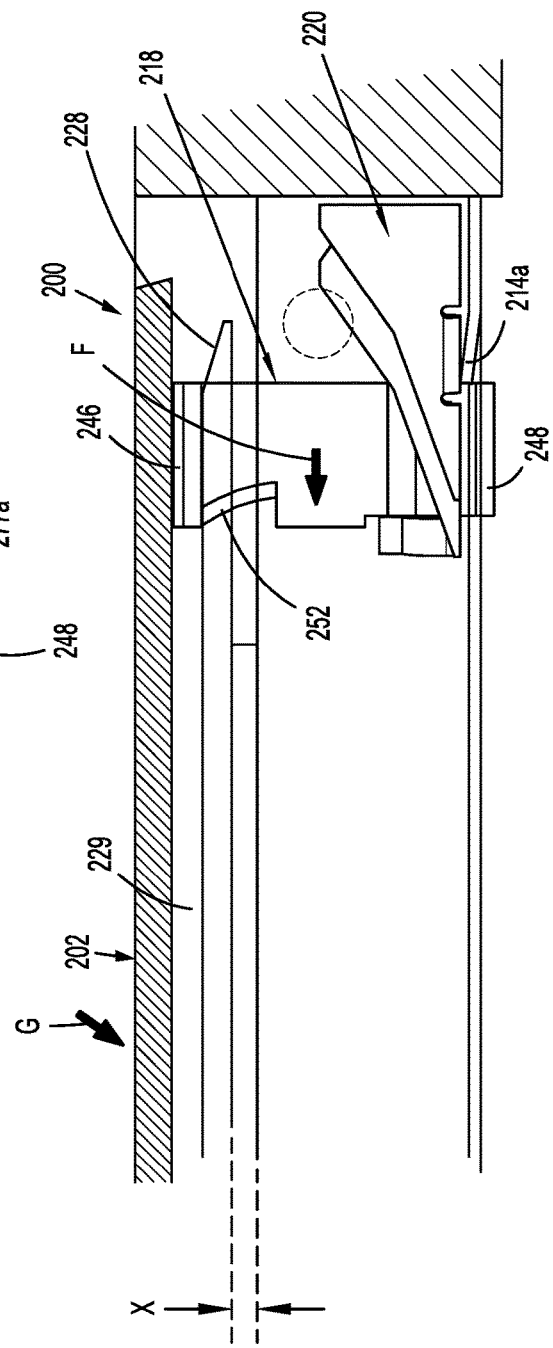

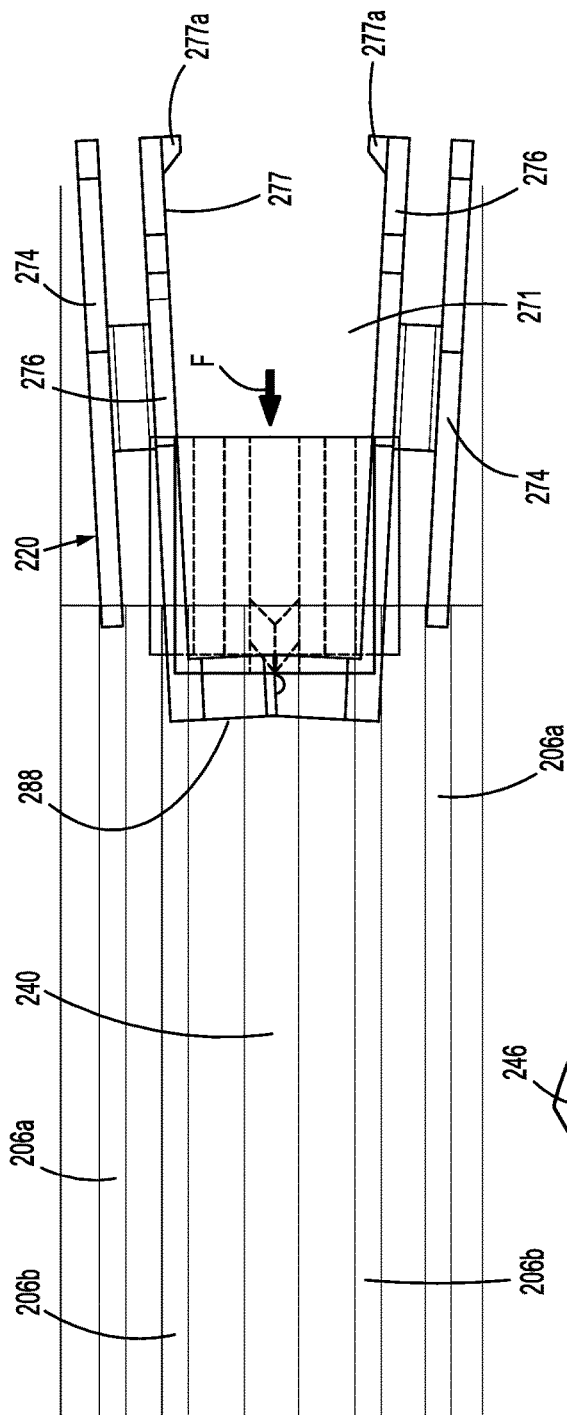
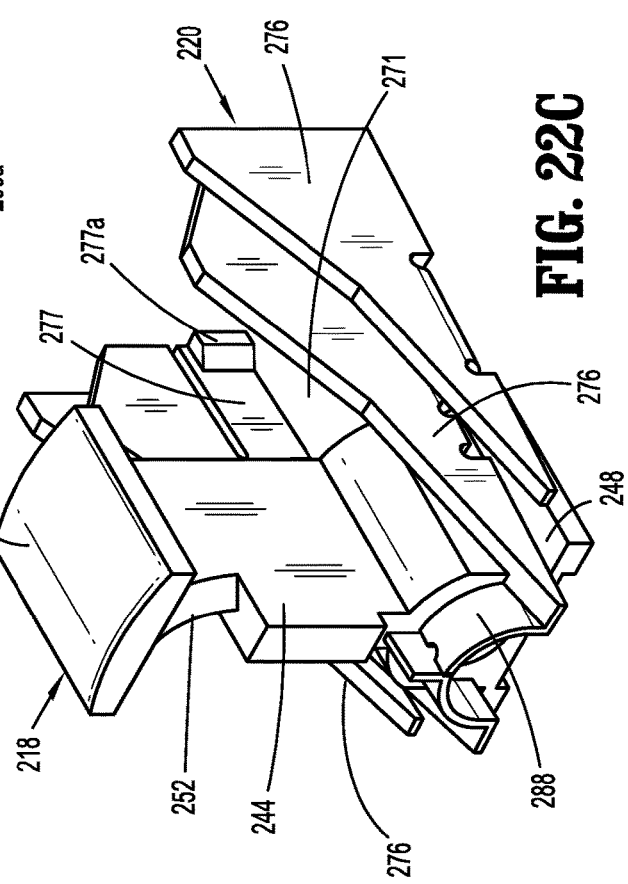

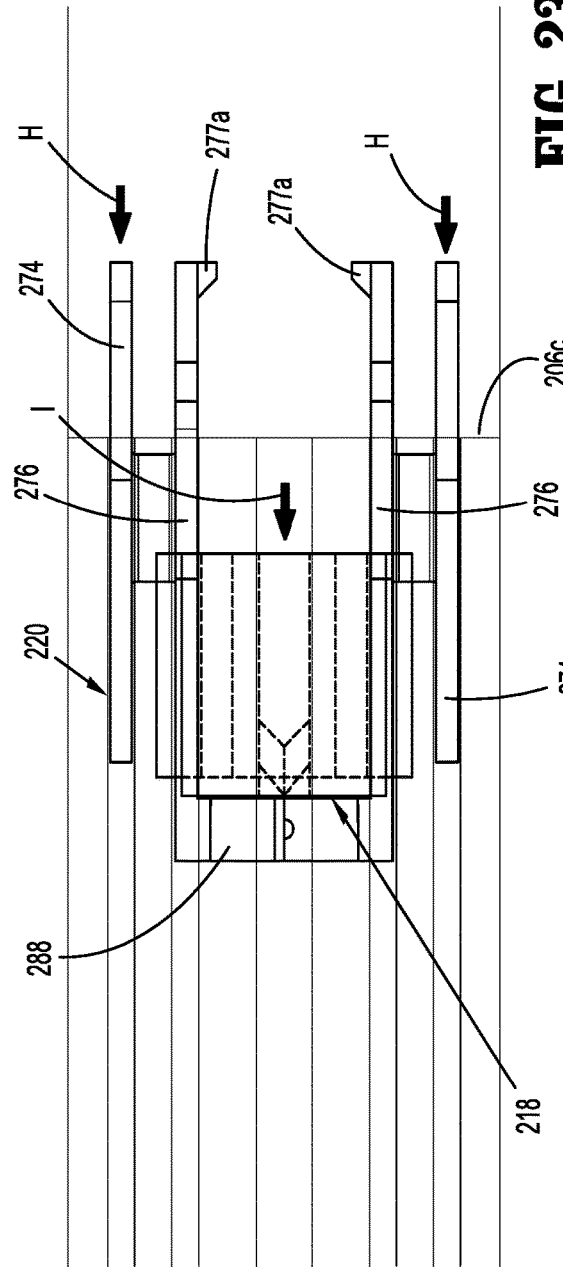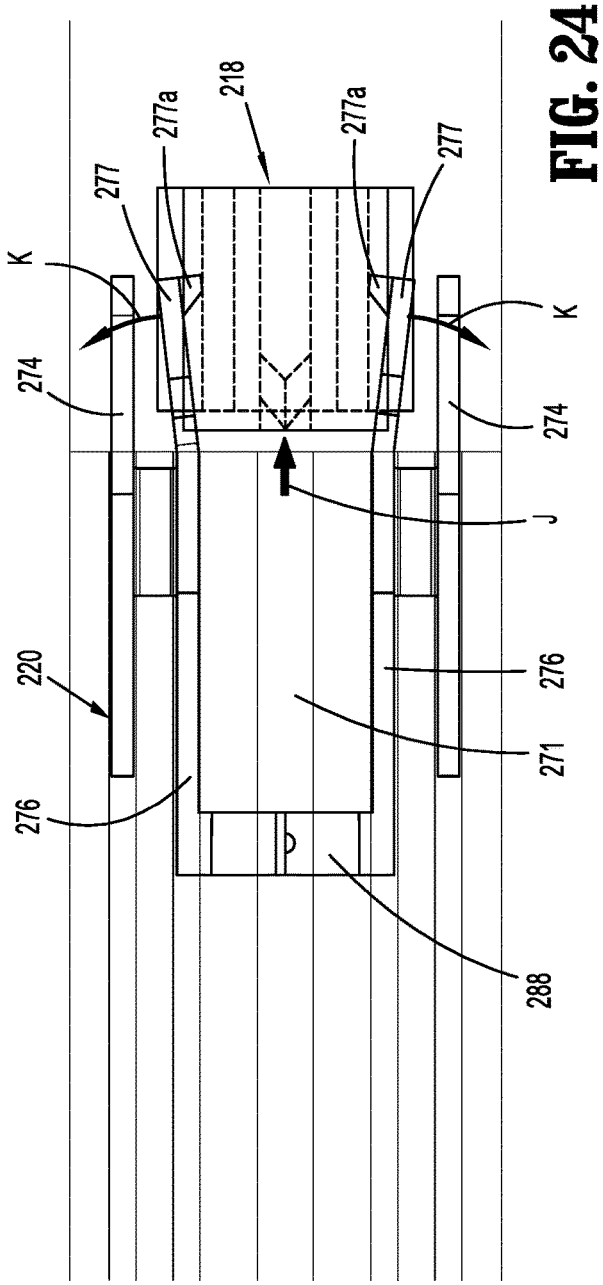

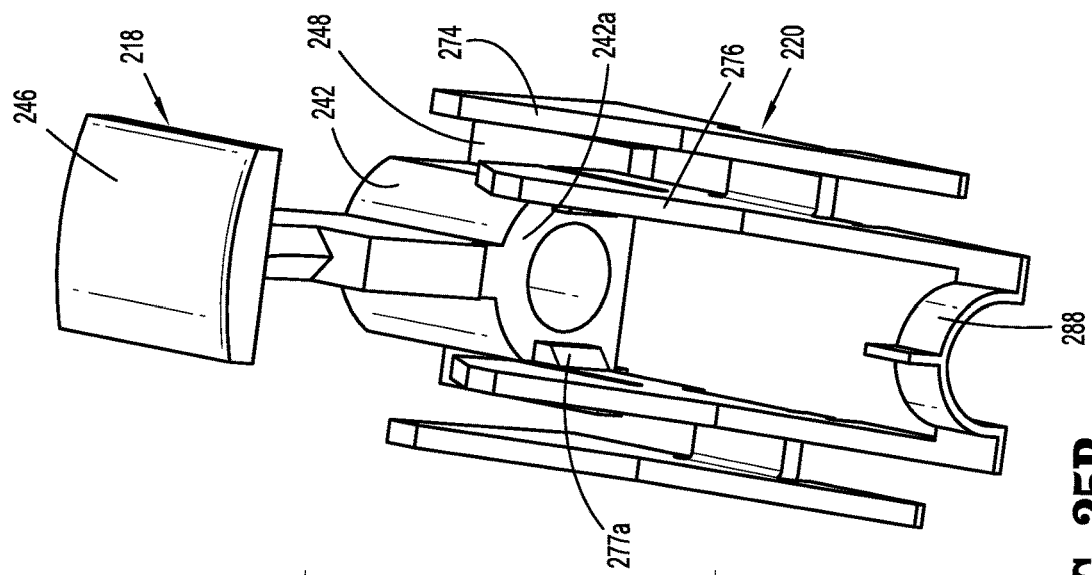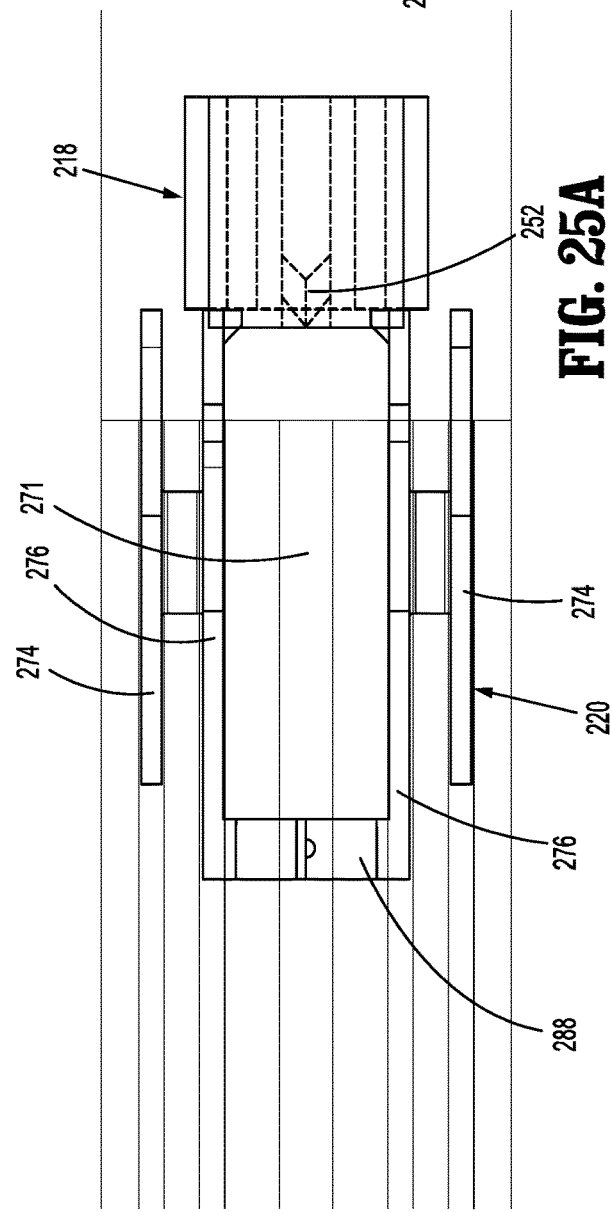
FIG. 25A
FIG. 25B

TOOL ASSEMBLY WITH MINIMAL DEAD SPACE

CROSS-REFERENCE TO RELATED APPLICATION

This application is a continuation of U.S. application Ser. No. 15/612,176, filed Jun. 2, 2017, the disclosure of which is incorporated herein by reference in its entirely.

BACKGROUND

1. Technical Description

The present disclosure is directed to a surgical stapling device and, more particularly, to an endoscopic surgical stapling device including an articulating tool assembly having an assembly including a knife clamp member and an actuation sled.

2. Background of Related Art

Surgical stapling devices for endoscopic use are known and include a tool assembly having a pair of jaws that are movable in relation to each other between open and clamped or approximated positions. Typically, one jaw of the tool assembly supports a staple cartridge having a plurality of staples and the other jaw of the tool assembly supports an anvil assembly. The tool assembly is supported on a distal portion of an elongate body of the surgical stapling device. In known stapling devices, the tool assembly is supported on the distal portion of the elongate body to improve access to tissue within a patient during an endoscopic surgical procedure.

Linear surgical stapling devices for endoscopic use include a drive member that supports a knife and an actuation sled. The actuation sled is positioned distally of the drive member within the staple cartridge and is driven by the drive member from a retracted position to an advanced position as the drive member is advanced through the staple cartridge. The actuation sled is configured to sequentially eject the staples from the staple cartridge as the actuation sled moves towards the advanced position. The jaws of the tool assembly may also include a tissue stop that prevents tissue from being positioned within a tissue gap defined by the pair of jaws at a location proximally of the location of the staples of the staple cartridge. The actuation sled is positioned distally of the knife of the drive member to facilitate formation of the staples in tissue prior to transection of the tissue.

Typically, the drive member includes clamping structure such as an I-beam to move the jaws of the tool assembly from an open position to an approximated or clamped position and to limit the size of the tissue gap defined between the jaws of the tool assembly. In such devices, since the drive member is positioned proximally of the actuation sled and proximally of the tissue stop, a proximal portion of the tool assembly includes a substantial amount of dead space, i.e., space on the tool assembly that is unusable for performing a stapling or cutting operation. In a surgical stapling device having a tool assembly that articulates, the dead space extends from an articulating axis or pivot point of the tool assembly to the tissue stop. This dead space increases the overall length of the tool assembly. The increased overall length of the tool assembly restricts access of the tool assembly to areas within a body cavity during an endoscopic surgical procedure.

It would desirable to minimize the length of the dead space of a tool assembly of an endoscopic surgical stapling device having an articulating tool assembly to provide improved access to tissue within a body cavity of a patient during an endoscopic surgical procedure.

SUMMARY

In one aspect of the disclosure, a surgical stapling device includes an elongate body and a tool assembly supported on a distal portion of the elongate body. The tool assembly includes a cartridge assembly and an anvil assembly that are movable in relation to each other between spaced and approximated positions. The cartridge assembly includes a staple cartridge supporting a plurality of staples, a clamp member having a body supporting a knife, and an actuation sled having a first portion and a second portion. Each of the first and second portions of the actuation sled defines a cam member. The second portion of the actuation sled is physically separated and spaced from the first portion of the actuation sled to define a channel between the first and second portions. In a pre-actuated state of the surgical stapling device, the clamp member is positioned within the channel defined between the first and second portions of the actuation sled such that the knife of the clamp member is positioned distally of a proximal end of the cam member of the first and second portions of the actuation sled. During at least a portion of a firing stroke of the surgical stapling device, the clamp member is movable to position the knife proximally of the cam members.

In embodiments, the cam member of each of the first and second portions of the actuation sled includes first and second cam members.

In some embodiments, the clamp member includes a vertical strut, an upper beam, and a lower beam, and in the pre-actuated state, the vertical strut is positioned within a proximal portion of the channel.

In certain embodiments, each of the first and second portions of the actuation sled includes an inner wall having a longitudinally extending portion and a transverse portion.

In embodiments, the longitudinally extending portion of the inner wall of each of the first and second portions of the actuation sled includes an inwardly extending resilient projection that extends into the channel into the path of the clamp member, wherein in the pre-actuated state, the clamp member is positioned to engage the resilient projections to urge the resilient projections from within the channel.

In some embodiments, the firing stroke includes a first advancement stage in which a distal surface of the clamp member is positioned to engage the transverse portion of the inner wall of the first and second portions of the actuation sled to move the actuation sled distally within the tool assembly.

In certain embodiments, the firing stroke includes a retraction stage in which the clamp member moves proximally within the channel to position the distal surface of the clamp member proximally of the resilient projections of the first and second portions of the actuation sled such that the resilient projections move into the channel.

In embodiments, the cartridge assembly includes a support plate having a resilient protrusion, wherein the actuation sled is positioned atop the resilient protrusion when the clamp member is in the pre-actuated state to urge the resilient protrusion from within the channel, and the actuation sled is positioned distally of the resilient protrusion when the stapling device is moved through the first advancement stage of the firing stroke such that the resilient protrusion prevents proximal movement of the actuation sled within the tool assembly during the retraction stage of the firing stroke.

In some embodiments, the clamp member has a base having opposed laterally extending flats that are positioned to engage the resilient projections in the pre-actuated state.

In certain embodiments, the base of the clamp member includes proximal stop members positioned at a proximal portion of the laterally extending flats.

In embodiments, the clamp member defines a threaded bore and the surgical stapling device further includes a threaded drive member, the threaded drive member being received within the threaded bore such that rotation of the threaded drive member causes axial movement of the clamp member.

In another aspect of the disclosure, a surgical stapling device includes an elongate body and a tool assembly supported on a distal portion of the elongate body. The tool assembly includes a cartridge assembly and an anvil assembly that are movable in relation to each other between spaced and approximated positions. The cartridge assembly includes a staple cartridge supporting a plurality of staples, a clamp member having a body supporting a knife, and an actuation sled having first and second spaced cam members. The first and second spaced cam members defining a channel there between. Each of the first and second cam members includes an inner cam member and an outer cam member. The inner cam members include a flexible portion supporting an inwardly extending protrusion, the flexible portion being flexible laterally to allow the clamp member to move proximally from within the channel to a position proximal of the channel.

In embodiments, the inwardly extending protrusions extend into the channel to obstruct movement of the clamp member within the channel.

In some embodiments, the inwardly extending protrusions have tapered distally facing surfaces.

In certain embodiments, in a pre-actuated state of the surgical stapling device, the clamp member is positioned within the channel of the actuation sled with the knife of the clamp member positioned distally of a proximal end of the first and second cam members of the actuation sled, wherein during at least a portion of a firing stroke of the surgical stapling device, the clamp member is movable to position the knife proximally of the first and second cam members.

In embodiments, the staple cartridge defines a longitudinal axis, a central knife slot extending along the longitudinal axis, and outer and inner cam slots positioned on each side of the central knife slot, wherein the outer and inner cam members are received in the outer and inner cam slots, respectively.

In some embodiments, in a pre-actuated state of the surgical device, the inner and outer cam members of the actuation sled extend beyond the proximal end of the inner and outer cam slots when the actuation sled is in the pre-actuated position such that the inner and outer cam members are angled outwardly in a direction away from the central knife slot to a position misaligned with the longitudinal axis of the staple cartridge.

In certain embodiments, the actuation sled includes a cross-member interconnecting a distal end of the inner cam members to each other.

In embodiments, the surgical stapling device is movable through a firing stroke, the firing stroke including a first advancement stage wherein a distal surface of the clamp member is positioned to engage the cross-member of the actuation sled to advance the actuation sled distally within the tool assembly.

In some embodiments, the firing stroke includes a retraction stage in which the clamp member moves proximally from within the channel into engagement with the inwardly extending protrusions on the flexible portions of the inner cam members to move the flexible portions to the misaligned position and allow the clamp member to move out of the channel of the actuation sled.

BRIEF DESCRIPTION OF THE DRAWINGS

Various embodiments of the presently disclosed surgical stapling device including a tool assembly with minimal dead space are described herein below with reference to the drawings, wherein:

FIG. 10 is a cross-sectional view taken along section line 10-10 of FIG. 1;

FIG. 11 is a perspective, cutaway view of the cartridge assembly of the tool assembly shown in FIG. 3 with the cartridge channel removed;

FIG. 11A is a cross-sectional view taken along section line 11A-11A of FIG. 11;

FIG. 12 is a side cross-sectional view of the cartridge assembly of the tool assembly shown in FIG. 2 in the approximated position;

FIG. 13 is a bottom perspective view of the cartridge assembly of the tool assembly shown in FIG. 3 with the cartridge channel removed and the tool assembly in the approximated position of the tool assembly;

FIG. 16 is a side cross-sectional view of the tool assembly shown in FIG. 15 as the tool assembly is moved through a second stage of the firing stroke;

FIG. 17 is a top, perspective view of the tool assembly shown in FIG. 16 showing the actuation sled and clamping member of the tool assembly with the remaining components of the tool assembly shown in phantom;

FIG. 21A is a side, cross-sectional view of a proximal portion of the tool assembly shown in FIG. 1 including the actuation sled and clamping member shown in FIG. 19 with the tool assembly in an unclamped position;

FIG. 21B is a top, schematic view of a cartridge assembly of the tool assembly shown in FIG. 21A;

FIG. 21C is a cross-sectional view taken along section line 21C-21C of FIG. 21B;

FIG. 21D is a side, perspective view from the proximal end of the actuation sled and clamping member shown in FIG. 19 assembled in the unclamped position;

FIG. 22A is a side cross-sectional view of the tool assembly of the surgical stapling device shown in FIG. 1 with the actuation sled and clamping member shown in FIG. 19 in the clamped position;

FIG. 22B is a top, schematic view of the tool assembly shown in FIG. 22A;

FIG. 22C is a side, perspective view from the distal end of the actuation sled and clamping member shown in FIG. 19 assembled in the clamped position;

FIG. 23 is a top, schematic view of the tool assembly shown in FIG. 22B as the tool assembly is moved through a first stage of a firing stroke;

FIG. 24 is a top, schematic view of the tool assembly shown in FIG. 22B as the tool assembly is moved through a second stage of the firing stroke;

FIG. 25A is a top, schematic view of the tool assembly shown in FIG. 24 after the tool assembly is moved through the second stage of the firing stroke;

FIG. 25B is a side, perspective view of the actuation sled and clamping member of the tool assembly shown in FIG. 25A.

DETAILED DESCRIPTION OF EMBODIMENTS

Figure 1:
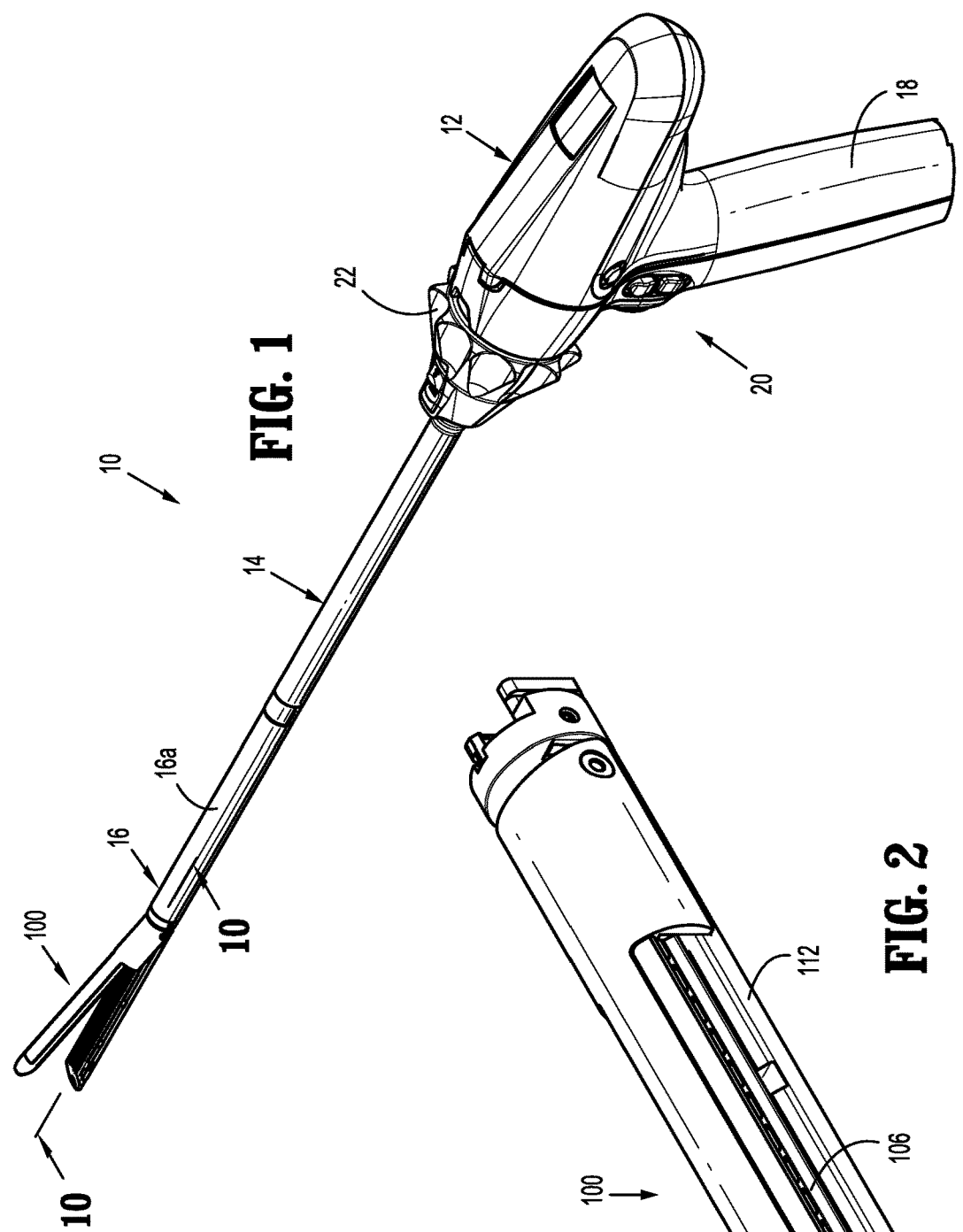
FIG. 1 is a side, perspective view of a surgical stapling device including one embodiment of the presently disclosed tool assembly in an open position.

The presently disclosed surgical stapling device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

The presently disclosed surgical stapling device includes a handle assembly, an elongate body extending distally from the handle assembly, and a tool assembly which is supported on a distal portion of the elongate body. In embodiments, the tool assembly is mounted onto the distal portion of the elongate body for articulation and includes a staple cartridge that supports a plurality of staples and pushers, an actuation sled that is movable through the staple cartridge to eject staples from the staple cartridge, and a drive or clamp member. The clamp member is movable through the tool assembly to move the tool assembly from an open position to an approximated position and to advance the actuation sled through the staple cartridge to eject the plurality of staples from the staple cartridge and to cut tissue. In order to minimize the length of the dead space in the proximal portion of the tool assembly, the actuation sled and clamp member are supported in a nested relationship within the staple cartridge when the tool assembly is in an unclamped or open position.

FIG. 1 illustrates a surgical stapling device 10 including a handle assembly 12, an elongate body 14, and an exemplary embodiment of the presently disclosed tool assembly 100. Although not described in detail herein, the tool assembly 100 can form part of a reload assembly 16 that includes a shaft portion 16a that supports the tool assembly 100 and is releasable from elongate body 14 as is known in the art. Alternately, the tool assembly 100 can be fixedly secured to a distal portion of the elongate body 14. The tool assembly 100 may or may not have a removable and replaceable staple cartridge assembly.

The handle assembly 12 includes a hand grip 18, a plurality of actuator buttons 20, and a rotation knob 22. The rotation knob 22 facilitates rotation of the elongate body 14 and the reload 100 about a longitudinal axis of the elongate body 14 in relation to the handle assembly 12 as is known in the art. The actuator buttons 20 control operation of the various functions of the stapling device 10 including approximation, firing and cutting. The stapling device 10 is illustrated as being an electrically powered stapling device such as described in U.S. Pat. No. 9,055,943 ("'943 Patent") which is incorporated herein by reference in its entirety. However, it is envisioned that the presently disclosed tool assembly 100 would also be suitable for use with manually powered surgical stapling devices such as described in U.S. Pat. No. 7,891,534 which is also incorporated herein by reference in its entirety. It is also envisioned that the stapling device 10 can be configured for use with a robotic surgical system and may not have a handle assembly.

Figure 2:
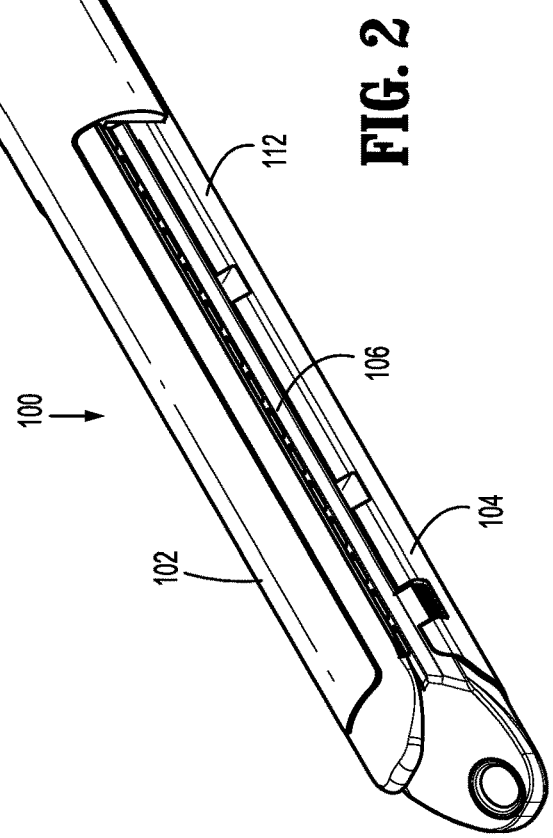
FIG. 2 is a side, perspective of the tool assembly shown in FIG. 1 in approximated position.
Figure 3:
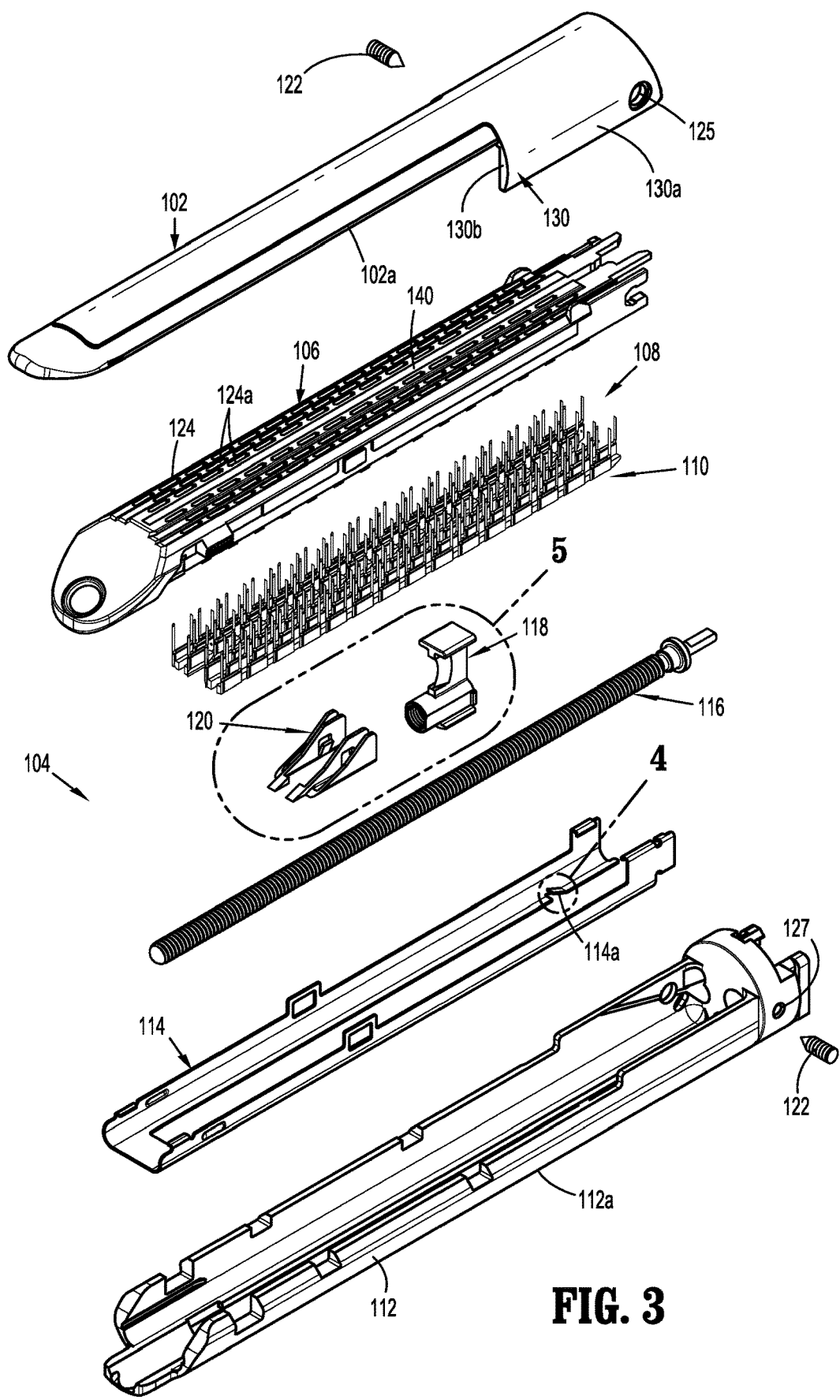
FIG. 3 is a side, perspective, exploded view of the tool assembly shown in FIG. 2.
Figure 4:
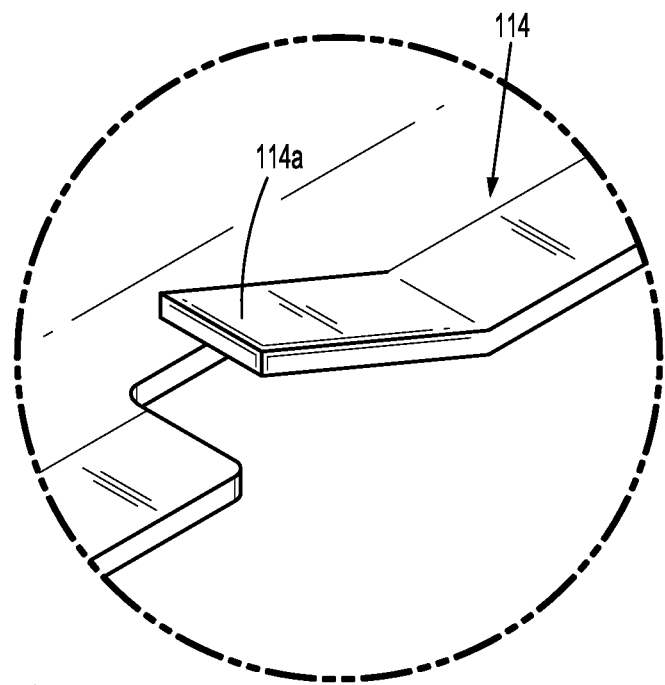
FIG. 4 is an enlarged view of the indicated area of detail shown in FIG. 3.
Figure 5:
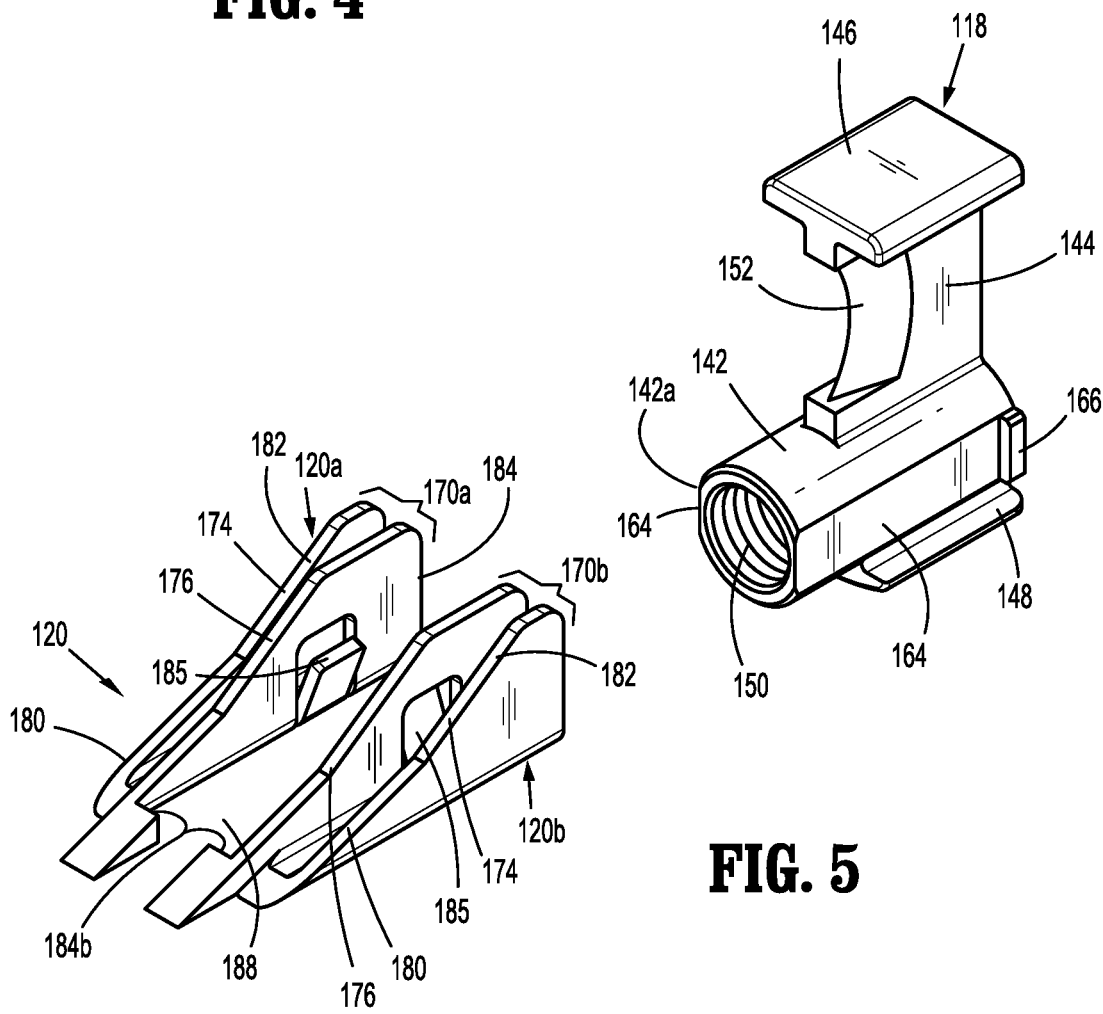
FIG. 5 is an enlarged view of the indicated area of detail shown in FIG. 3.
Figure 6:
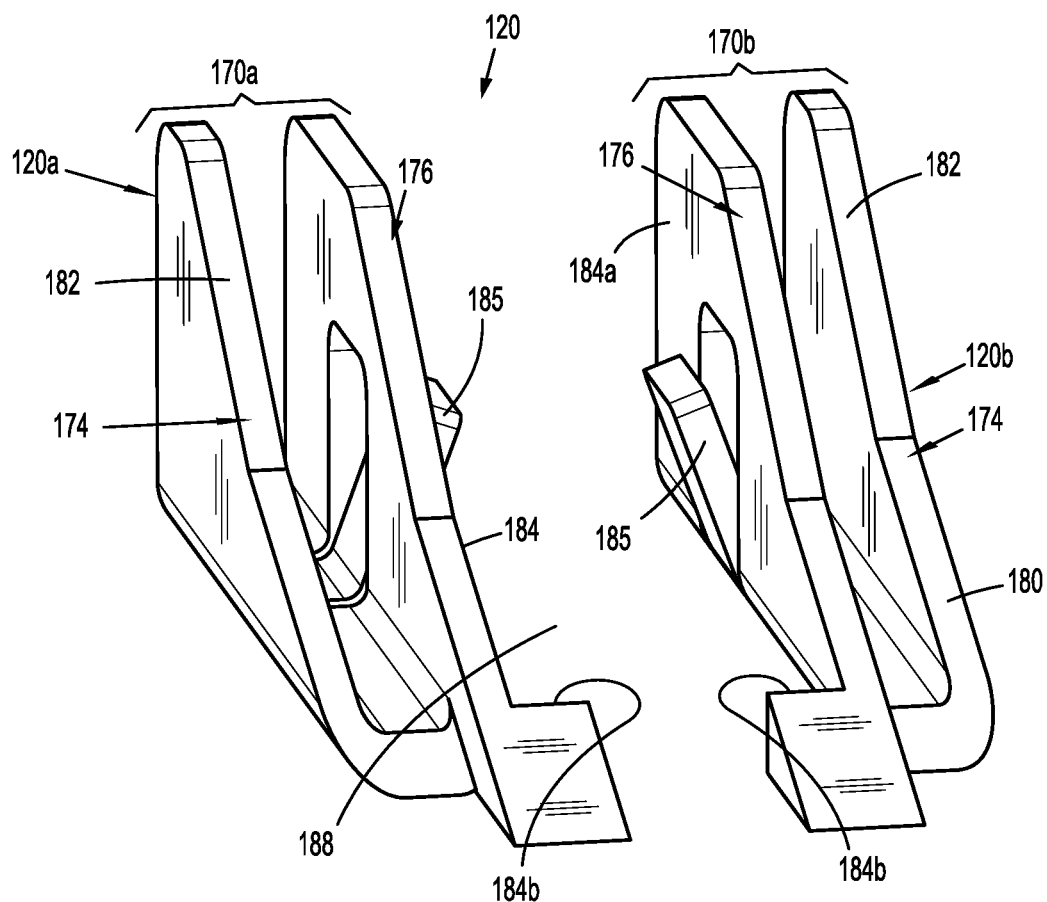
FIG. 6 is a perspective view from the distal end of an actuation sled of the tool assembly shown in FIG. 5.
Figure 7:
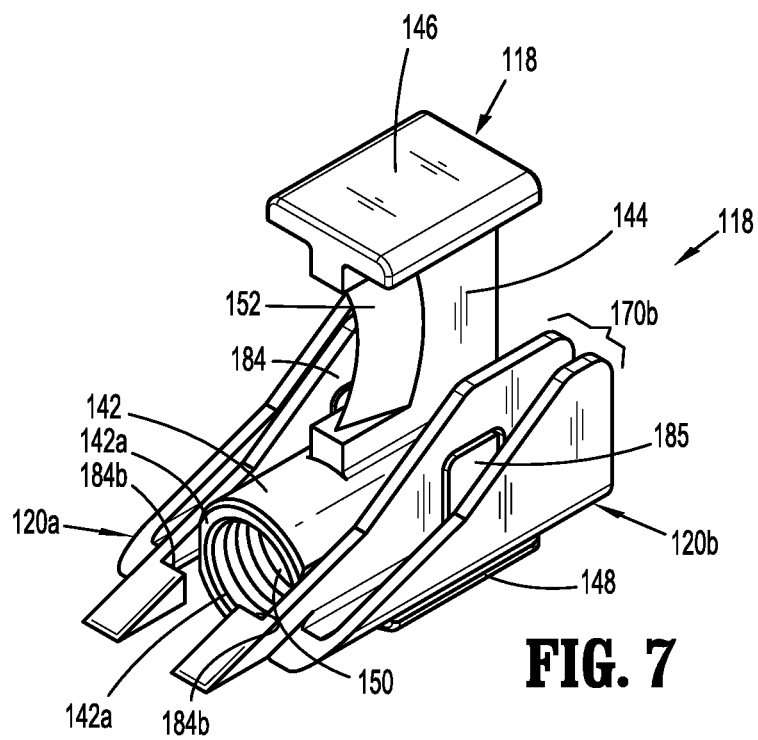
FIG. 7 is a side, perspective view from the distal end of the actuation sled and clamping member of the tool assembly shown in FIG. 5.
Figure 8:
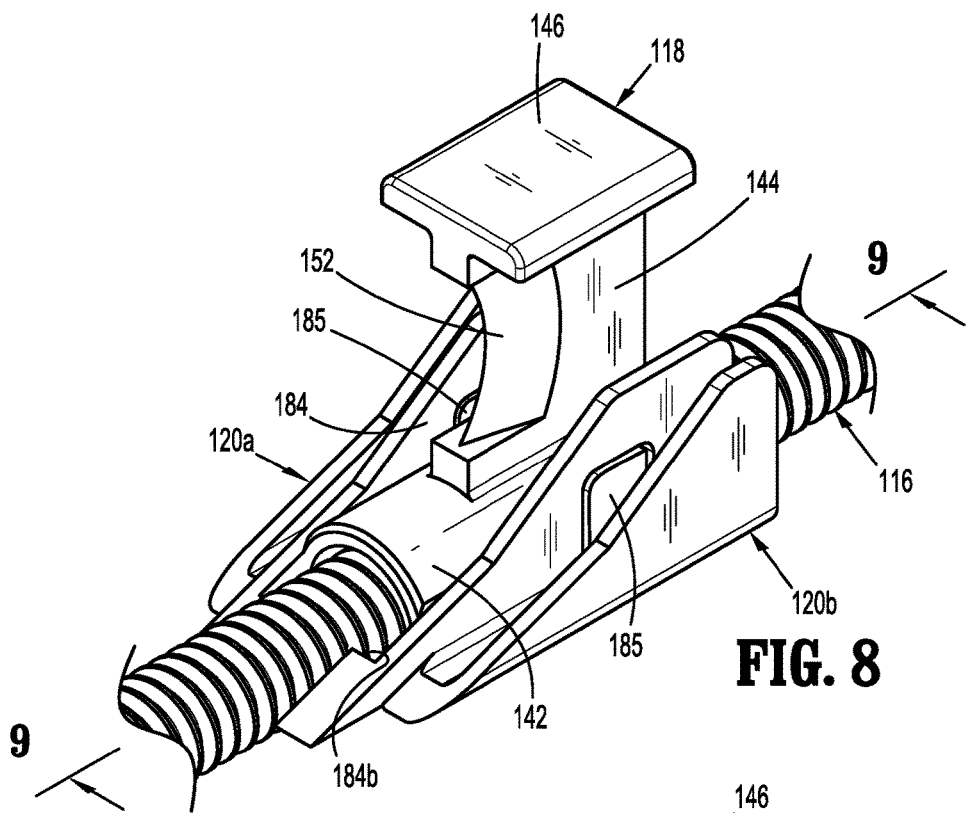
FIG. 8 is a side, perspective view of the clamp member and actuation sled shown in FIG. 7 supported on a drive screw of the tool assembly shown in FIG. 3.
Figure 9:
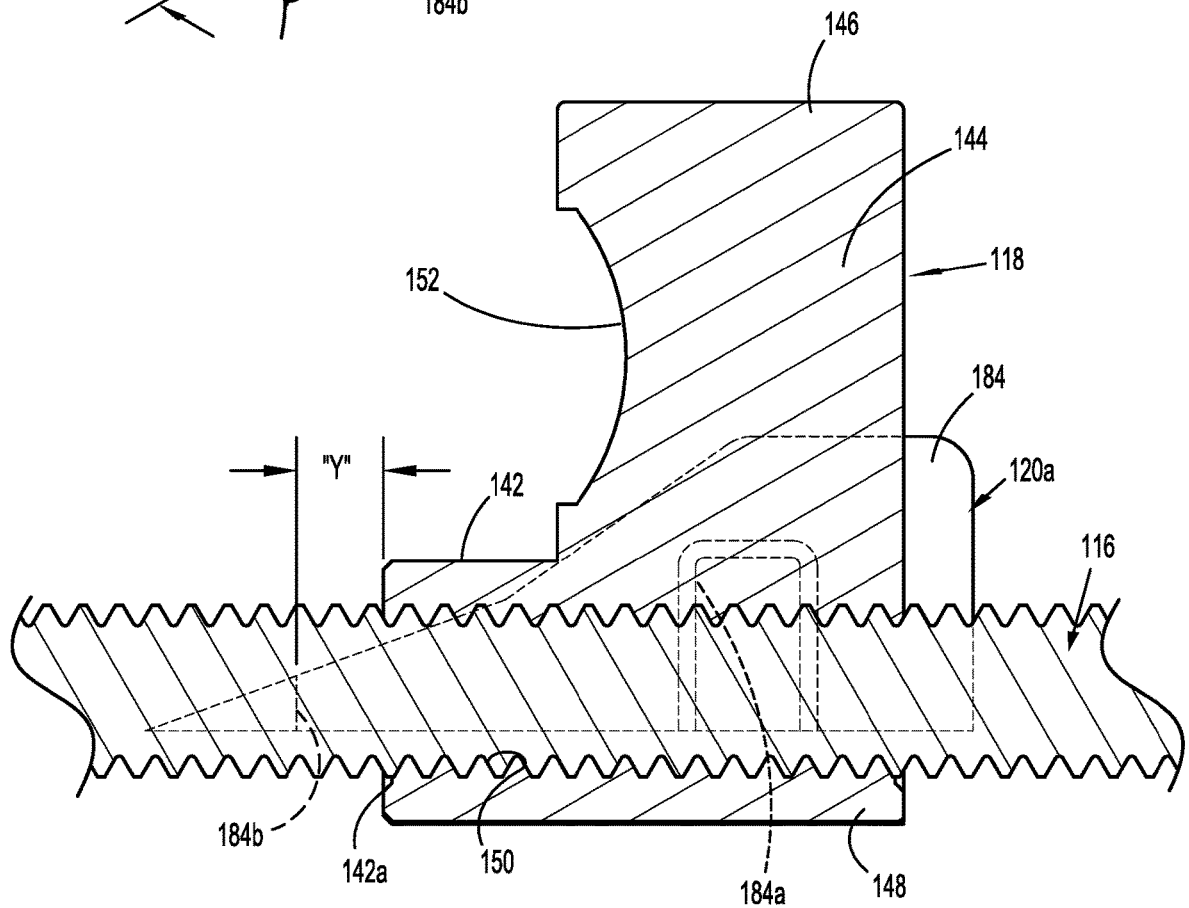
FIG. 9 is a cross-sectional view taken along section line 9-9 of FIG. 8.

Referring to FIGS. 2-4, the tool assembly 100 includes an anvil 102 and a cartridge assembly 104. The cartridge assembly 104 includes a staple cartridge 106 that supports a plurality of staples 108 and pushers 110 (FIG. 3), a cartridge channel 112 defining a bottom surface 112a, a staple cartridge support plate 114, a drive screw 116, a clamp member 118, and an actuation sled 120. The support plate 114 includes a resilient protrusion, e.g., a resilient lance 114a (FIG. 4), that defines a stop surface for the actuation sled 120 as described in further detail below. Alternatively other protrusion configurations are envisioned. The staple cartridge 106 defines a central knife slot 140 (FIG. 3) and is attached within the support plate 114 by a snap-fit connection. The support plate 114 and staple cartridge 106 are assembled together and attached to the cartridge channel 112 also by a snap-fit connection. Alternately, other techniques for securing these components together may be used.

Referring to FIG. 3, the staple cartridge 106 includes a tissue contact surface 124 that defines a plurality of rows of laterally spaced staple retention slots 124a. The retention slots 124a are configured as holes in the tissue contacting surface 124. Each retention slot 124a receives one of the staples 108 and at least a portion of a respective one of the pushers 110. The staple cartridge 106 also defines a plurality of longitudinal cam slots 106a (FIG. 11A). The longitudinal cam slots 106a accommodate the staple pushers 110 (FIG.

11) and are open on an end opposite to the tissue-contacting surface 124 to facilitate passage of the actuation sled 120.

The anvil 102 is pivotally coupled to the cartridge assembly 104 about pivot members 122. The pivot members 122 extend through openings 125 (FIG. 3) defined in a proximal portion of the anvil 102 and openings 127 defined in a proximal portion of the cartridge assembly 106. The anvil 102 is pivotal in relation to the cartridge assembly 106 to transition the tool assembly 100 between an open position (FIG. 1) and an approximated position (FIG. 2). The anvil 102 includes a tissue contact surface 102a (FIG. 10) that defines a plurality of staple deforming depressions (not shown) as is known in the art. The anvil 102 also defines a channel 129 (FIG. 10) and includes a ramped abutment surface 128 (FIG. 10) and a tissue stop 130. The ramped abutment surface 128 is positioned adjacent a proximal end of the channel 129 and is engaged by the clamp member 118 to facilitate movement of the tool assembly 100 from the open position to the approximated position. In embodiments, the tissue stop 130 includes a pair of downwardly extending wings 130a positioned on opposite sides of the tissue contact surface 102a of the anvil 102. Each of the wings 130a has a distal tissue engaging surface 130b that extends below the tissue contact surface 124 of the staple cartridge 106 when the tool assembly 100 is in the open position. The distal engaging surface 130b of the tissue stop 130 prevents tissue from passing between the anvil and cartridge assemblies 102, 104 of the tool assembly 100 proximally beyond the staple retention slots 124a.

Referring also to FIGS. 5-9, the clamp member 118 includes a base 142 having a distal surface 142a, a vertical strut 144, an upper beam 146, and a lower beam 148. The vertical strut 144 has a first end secured to the base 142 and a second end secured to the upper beam 146. In some embodiments, the base 142 is substantially cylindrical and defines a threaded bore 150 that rotatably receives the drive screw 116 (FIG. 3). In embodiments, the base 142 includes opposed longitudinally extending flats 164 and proximal stop members 166 that are discussed in further detail below. In some embodiments, the drive screw 116 (FIG. 9) is threaded and is received within the threaded bore 150 of the clamp member 118 to translate rotational movement of the drive screw 116 into longitudinal movement of the clamp member 118.

The vertical strut 144 includes a distal surface that defines a knife 152 that is positioned between the upper and lower beams 146, 148. The upper beam 146 is positioned to engage the ramped abutment surface 128 (FIG. 10) of the anvil assembly 102 such that movement of the clamp member 118 from a retracted position to a clamped position transitions the tool assembly 100 from the open position (FIG. 10) to the approximated position (FIG. 12). The upper beam 146 is also positioned to translate through the channel 129 (FIG. 10) defined in the anvil assembly 102 and the lower beam 148 is positioned to translate along the bottom surface 112a (FIG. 10) of the cartridge channel 112 to prevent outward deflection of the anvil 102 and the cartridge assembly 104 during firing of the stapling device 10. The upper and lower beams 146, 148 are dimensioned to allow for a maximum tissue gap "X" (FIG. 12) between the tissue contact surface 102a of the anvil assembly 102 and the tissue contact surface 124 of the staple cartridge 106 during firing of the tool assembly 100.

The actuation sled 120 includes a first portion 120a including a first pair of spaced cam members 170a and a second portion 120b including a second pair of spaced cam members 170b. The first and second portions 120a and 120b of the actuation sled 120 may be separate components as shown. Alternately, the first and second portions of the actuation sled 120 can be joined at their proximal and/or distal ends to each other. Each pair of spaced cam members 170a, 170b is positioned to translate through a respective longitudinal cam slot 106a (FIG. 11A) defined by the staple cartridge 106 to interact with the pushers 110 (FIG. 3) and eject staples 108 from the staple cartridge 106 as is known in the art. In embodiments, each of the pair of spaced cam members 170a, 170b includes two spaced cam surfaces 174, 176 that sequentially engage the pushers 110 (FIG. 3) as the actuation sled 120 translates through the staple cartridge 106 to lift the pushers 110 within the staple retention slots 124a of the staple cartridge 106 and eject the staples 108 from the staple retention slots 124a of the staple cartridge 106. The angle of the cam surfaces 174, 176 may vary along the length of the cam surfaces 174, 176 to better control movement of the pushers 108 through the staple retention slots 124a and provide better staple formation. For example, the cam surfaces 174, 176 may have a distal portion 180 and a proximal portion 182 wherein the proximal portion 182 is steeper than the distal portion 180.

Referring also to FIGS. 5-11A, each of the first and second portions 120a, 120b of the actuation sled 120 includes an inner wall 184 with a longitudinally extending portion 184a having an inwardly extending resilient projection 185 (FIG. 6), and a transverse portion 184b. When the first and second portions 120a, 120b of the actuation sled 120 are positioned within the staple cartridge 106, the first and second portions 120a and 120b define a channel 188 that is positioned to receive the base 142 of the clamp member 118 such that the clamp member 118 is movable within the channel 188 from a retracted position to an advanced position. In an unbiased state, the resilient projections 185 extend inwardly into the channel 188. The transverse portions 184b of the first and second portions 120a, 120b of the actuation sled 120 define a distal end of the channel 188 and are positioned to engage the distal surface 142a (FIG. 5) of the clamp member 118 when the clamp member 118 is moved to the advanced position within the channel 188. The actuation sled 118 and the clamp member 120 form an assembly in which the first and second portions 120a, 120b of the actuation sled 120 are disposed alongside the clamp member 120 including the knife 152.

When the base 142 of the clamp member 118 is positioned between the first and second portions 120a, 120b of the actuation sled 120 (FIG. 8), the flats 164 (FIG. 5) of the base 142 are aligned with the resilient projections 185 of the actuation sled 120 to bias and retain the resilient projections 185 in alignment with a respective one of the inner walls 184 of the first and second portions 120a, 120b of the actuation sled 120. When the resilient portions 185 are biased inwardly from the channel 188, the clamp member 118 is free to move through the channel 188 and into engagement with the transverse portions 184b of the inner wall 184 of the first and second portions 120a, 120b of the actuation sled 120. When the clamp member 118 is moved within the channel 188 in relation to the actuation sled 120 such that the flats 164 are positioned proximally of the resilient projections 184a as discussed below, the resilient projections 185 spring into the channel 188 defined between the first and second portions 120a, 120b of the actuation sled 120 to a position aligned with the distal surface 142a (FIG. 5) of the clamp member 118. As such, distal movement of the clamp member 118 beyond the resilient projections 185 is prevented.

Referring to FIGS. 8-11A, when the surgical stapling device 10 is in a pre-actuated state, the clamp member 118 and the actuation sled 120 are in a nested configuration. In the nested configuration, the clamp member 118 is positioned between the first and second portions 120a and 120b of the actuation sled 120 within the channel 188 (FIG. 6) such that the distal surface 142a of the base member 142 of the clamp member 118 is positioned proximally a distance "Y" (FIG. 9) from the transverse portions 184b of the inner walls 184 of the first and second portions 120a, 120b of the actuation sled 120. In this position, the flats 164 (FIG. 5) of the base member 142 (FIG. 6A) are aligned with the resilient projections 185 of the inner wall 184 of the actuation sled 120 such that the projections 185 are urged out of the channel 188 of the actuation sled 120. In addition, the actuation sled 120 is positioned atop the lance 114a (FIG. 10) of the support plate 114 of the cartridge assembly 104 to urge the lance 114a out of the channel 188 defined between the first and second portions 120a, 120b of the actuation sled 120.

The drive screw 116 extends through the threaded bore 150 of the clamp member 118 and includes a proximal portion "P" (FIG. 10) supported on a bearing and that is coupled to a drive member (not shown) supported within the elongate body 114 (FIG. 1) of the surgical stapling device 10. U.S. Pat. No. 8,512,359 discloses a surgical stapling device including a drive screw and drive member and is incorporated herein in its entirety by reference.

Figure 14:
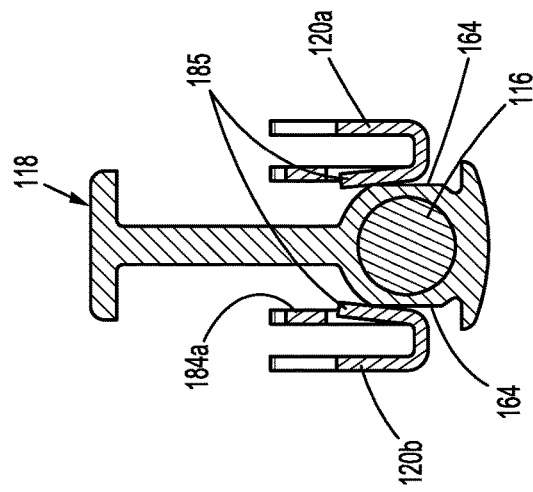
FIG. 14 is a cross-sectional view taken along section line 14-14 of FIG. 12.

Referring to FIGS. 12-14, when the drive screw 116 is actuated via the handle assembly 12 (FIG. 1) and the elongate body 14 (FIG. 1) to advance the clamp member 118 through a clamping stroke of the surgical stapling device 10, the clamp member 118 moves from a retracted position to a clamped position. As the clamp member 118 moves towards the clamped position, the clamp member 118 moves along the drive screw 116 distally through the channel 188 defined between the first and second portions 120a, 120b of the actuation sled 120 independently of the actuation sled 120. As the clamp member 118 moves distally within the proximal portion of the tool assembly 100, the upper beam 146 of the clamp member 118 engages the ramped abutment surface 128 (FIG. 12) of the anvil assembly 102 such that continued distal movement of the clamp member 118 in the direction indicated by arrow "A" in FIG. 12 to the clamped position pivots the anvil assembly 102 in the direction indicated by arrow "B" in FIG. 12 to urge the tool assembly 100 from the open position (FIG. 10) to the approximated position. It is envisioned that the anvil assembly 102 may be stationary and the cartridge assembly 104 may pivot in relation to the anvil assembly 102 from the open position to the approximated position.

When the clamp member 118 is in the clamped position, the distal surface 142a (FIG. 12) of the base 142 of the clamp member 118 is positioned adjacent the transverse portions 184b of the inner walls 184 of the first and second portions 120a, 120b of the actuation sled 120. In this position, the flats 164 of the base member 142 (FIG. 11A) are still aligned with the resilient projections 185 of the inner wall 184 of the actuation sled 120 such that the resilient projections 184a are positioned outwardly of the channel 188 of the actuation sled 120. In addition, the tool assembly 100 is in the approximated position with the tissue contact surface 124 of the cartridge assembly 106 positioned in juxtaposed alignment with the tissue contact surface 102a of the anvil assembly 102 to define a maximum tissue gap "X" (FIG. 12). The actuation sled 120, which has not moved within the tool assembly 100, remains positioned atop the lance 114a of the support plate 114 of the cartridge assembly 104.

In order to eject staples 108 (FIG. 3) from the tool assembly 100, the drive member 116 is actuated again via the handle assembly 12 and the elongate body 14 (FIG. 1) to move the clamp member 118 through a firing stroke. During the firing stroke, the clamp member 118 and the actuation sled 120 are moved through a first advancement stage shown in FIG. 15, through a retraction stage shown in FIGS. 16 and 17, and through a second advancement stage shown in FIG. 18. Each of these stages is described below.

Figure 15:
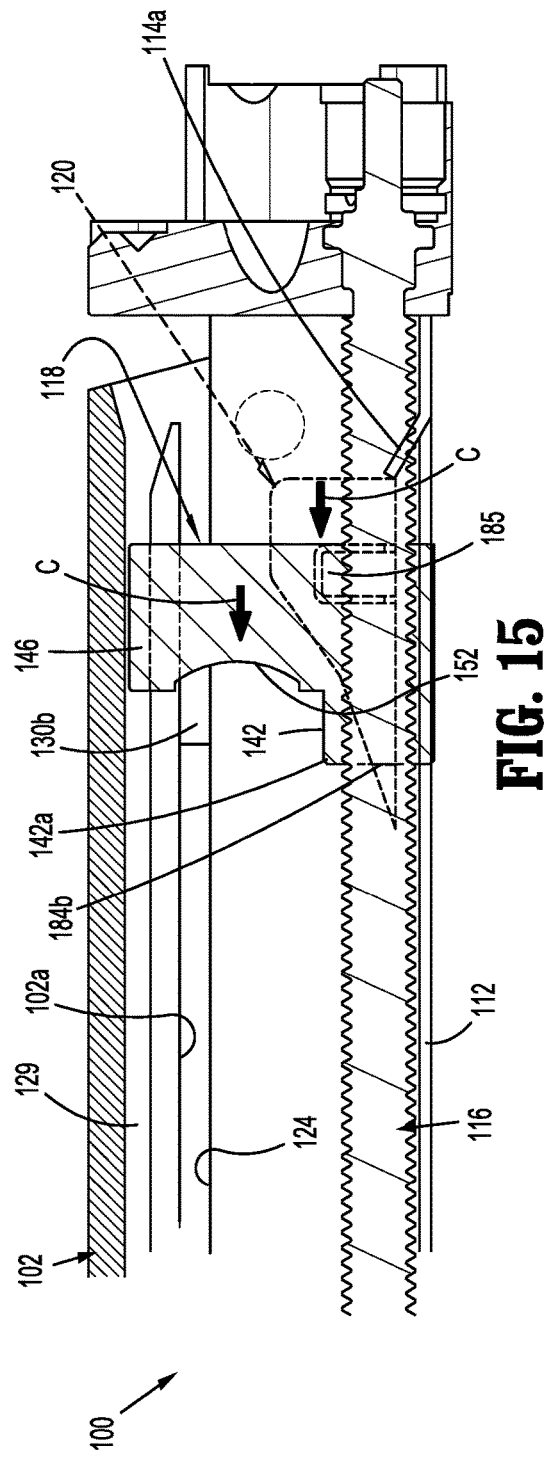
FIG. 15 is a side cross-sectional view of the tool assembly shown in FIG. 12 as the tool assembly is moved through a first stage of a firing stroke.

Referring to FIG. 15, during the first advancement stage of the firing stroke, the drive screw 116 initially advances the clamp member 118 in the direction indicated by arrows "C" distally from the clamped position. As discussed above, in the clamped position the distal surface 142a of the base 142 of the clamp member 118 is positioned adjacent the transverse portions 184b of the inner walls 184 of the first and second portions 120a, 120b of the actuation sled 120. As such, when the clamp member 118 moves distally within the tool assembly 100 from the clamped position, the distal surface 142a of the clamp member 118 engages the transverse portions 184b of the actuation sled 120 to advance the actuation sled 120 distally within the cartridge 106. When the actuation sled 120 is advanced past the lance 114a, the lance 114a flexes upwardly into the path of the actuation sled 120 and the first advancement stage of the firing stroke ends.

Referring to FIGS. 16 and 17, during the retraction stage of the firing stroke, the drive screw 116 is rotated in an opposite direction to that of the rotational direction of the drive screw 116 in the first stage of the firing stroke to retract the clamp member 118 within the tool assembly 100 in the direction indicated by arrows "D". The lance 114a which is positioned within the channel 118 of the actuation sled 120 engages a proximal end of the actuation sled 120 to prevent proximal movement of the actuation sled 120 with the clamp member 118. As such, the clamp member 118 moves proximally independently of the actuation sled 118 within the tool assembly 100. As the clamp member 118 moves proximally, the distal surface 142a of the clamp member 118 passes over the resilient projections 185 of the actuation sled 120 such that the resilient projections 185 spring outwardly into the channel 188 of the actuation sled 120 to prevent distal movement of the clamp member 118 through the channel 188 beyond the resilient projections 184. By moving and retaining the clamp member 118 further proximally of the actuation sled 120, the tool assembly 100 is reconfigured to position the cam surfaces 174, 176 of the actuation sled 120 distally of the knife 152 such that the tool assembly 100 staples tissue prior to cutting tissue.

Figure 18:
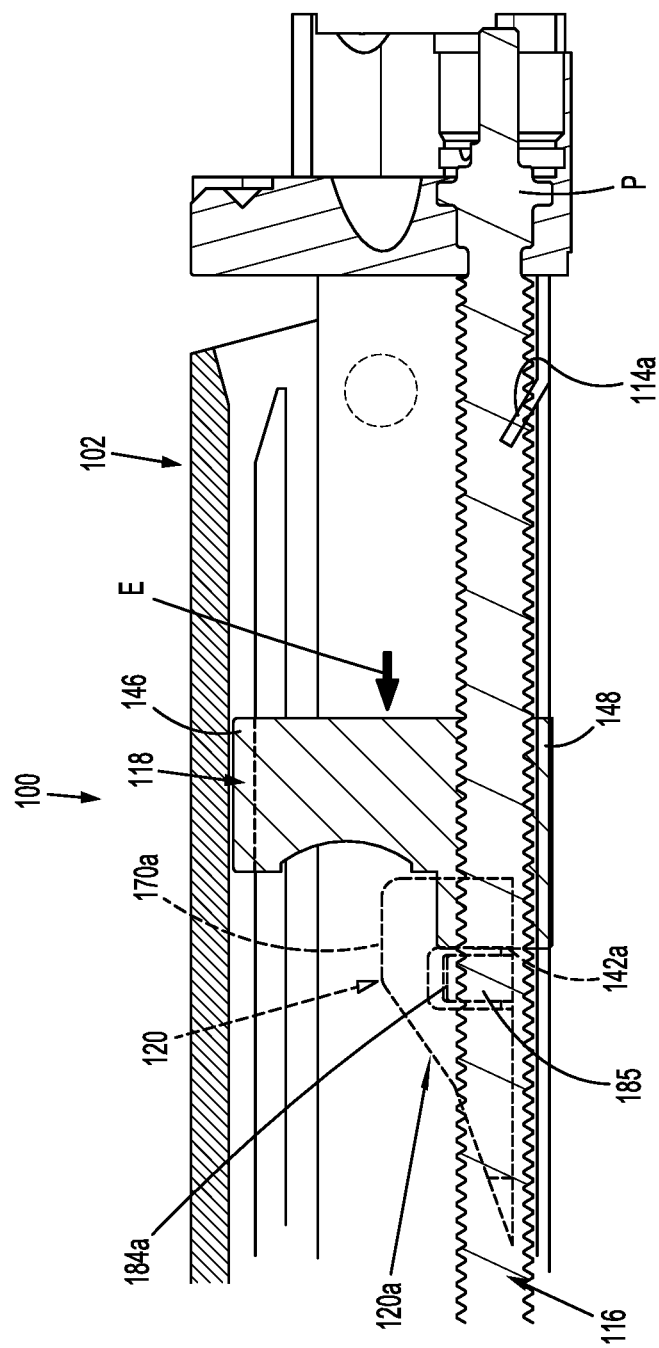
FIG. 18 is a side cross-sectional view of the tool assembly shown in FIG. 16 as the tool assembly is moved through a third stage of the firing stroke.

Referring to FIG. 18, after the retraction stage of the firing stroke, the distal surface 142a of the base 142 of the clamp member 118 is positioned proximally of the resilient projections 185 of the actuation sled 120. During the second advancement stage of the firing stroke, the drive screw 116 is rotated to advance the clamp member 118 distally in the direction indicated by arrow "E" through the tool assembly 100. Since the distal surface 142a of the base 142 of the clamp member 118 is positioned slightly proximally of the resilient projections 185 of the actuation sled 120, distal movement of the clamp member 118 causes the distal surface 142a of the clamp member 118 to move into engagement with the resilient projections 185 to move the actuation sled 120 distally within the tool assembly 100. As the actuation sled 120 and the clamp member 118 are advanced through the tool assembly 100, the pair of spaced cam members 170a, 170b of the first and second portions 120a, 120b of the actuation sled 120 sequentially engage the pushers 110 (FIG. 3) to sequentially drive the staples 108 from the staple retention slots 124a (FIG. 17).

After the second advancement stage of the firing stroke, the tool assembly can be withdrawn from the surgical site and the drive screw 116 can be rotated to retract the clamp member 118 to it pre-fired state. When the clamp member 118 returns to the pre-fired state, the tool assembly is returned to the open position.

Figure 19:
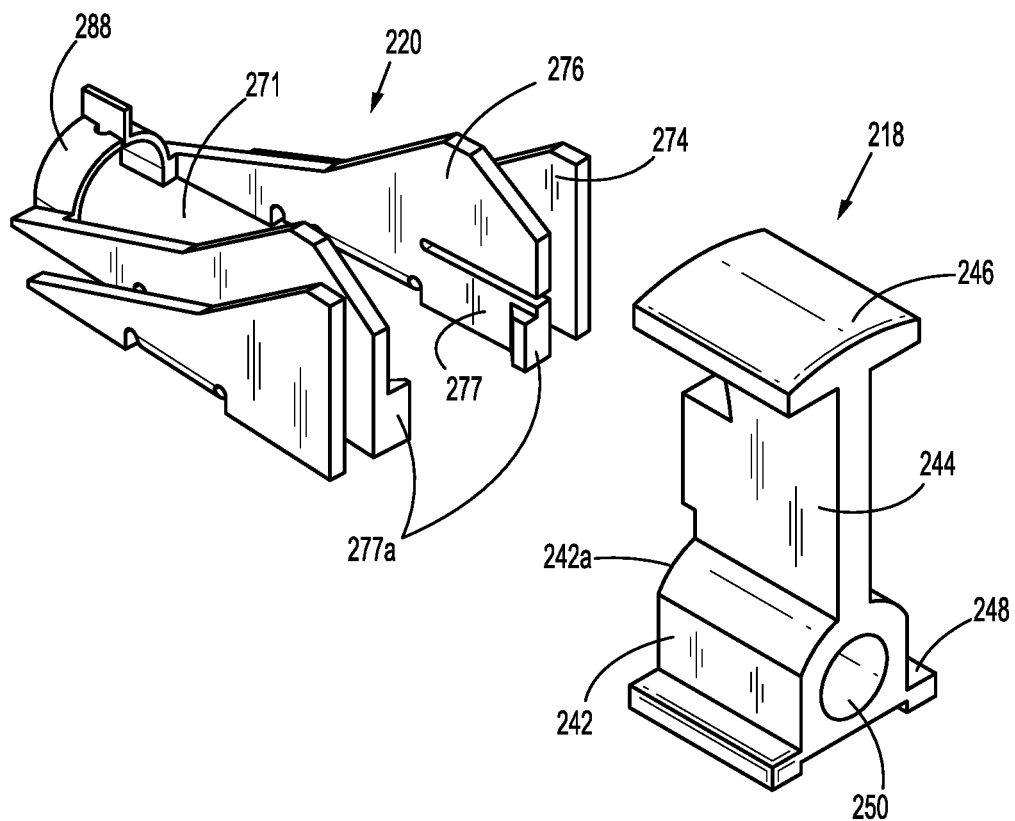
FIG. 19 is a side perspective view from the proximal end of another embodiment of an actuation sled and clamping member of the presently disclosed surgical stapling device shown in FIG. 1 with parts separated.
Figure 20:
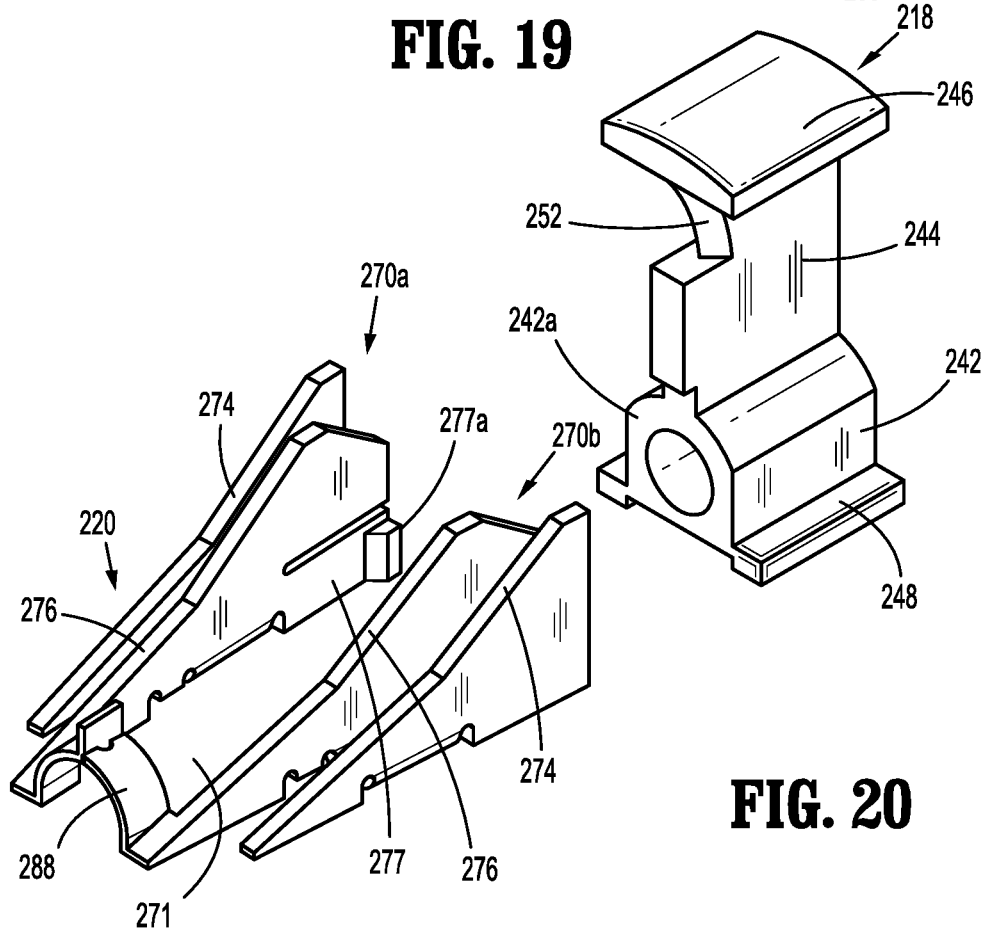
FIG. 20 is a side perspective view from the distal end of the actuation sled and clamping member shown in FIG. 19 with parts separated.

FIGS. 19 and 20 illustrate an alternate embodiment of the presently disclosed clamp member 218 and actuation sled 220 which can be used with the surgical stapling device shown in FIG. 1. The clamp member 218 includes a base 242, a vertical strut 244, an upper beam 246, and a lower beam 248. The vertical strut 244 has a first end secured to the base 242 and a second end secured to the upper beam 246. In embodiments, the base 242 defines a threaded bore 250 that rotatably receives a drive screw 116 (FIG. 3). As discussed above in regard to tool assembly 100, the drive screw 116 is threaded and is rotatable within the threaded bore 250 of the clamp member 218 to translate the rotational movement of the drive screw 116 into longitudinal movement of the clamp member 218 within a tool assembly 200 (FIG. 21A).

Referring also to FIG. 21A, the vertical strut 244 of the clamp member 218 includes a distal surface that defines a knife 252 that is positioned between the upper and lower beams 246, 248. The upper beam 246 is positioned to engage an abutment surface 228 of an anvil assembly 202 of the tool assembly 200 such that movement of the clamp member 218 from a retracted position (FIG. 21A) to a clamped position (FIG. 22A) moves the tool assembly 200 from the open position to the approximated position. As discussed above in regard to the tool assembly 100, the upper beam 246 of the clamp member 218 is positioned to translate through a channel 229 (FIG. 21A) defined in the anvil assembly 202 and the lower beam 248 is positioned to translate along the bottom surface 212a (FIG. 21A) of a cartridge channel 212 of a cartridge assembly 204 to define a maximum tissue gap "X" (FIG. 22A) between a tissue contact surface 202a of the anvil assembly 202 and a tissue contact surface 224 of the staple cartridge 206 of the tool assembly 200 when the tool assembly 200 is in the approximated position. The base 242 of the clamp member 218 also includes a distal surface 242a (FIG. 19) that is positioned to engage and advance the actuation sled 220 as described in further detail below.

The actuation sled 220 includes cam members 270a, 270b (FIG. 20) that are substantially similar to the spaced cam members 170a, 170b described above in regard to the actuation sled 120 and will not be described in further detail herein. The cam members 270a, 270b are spaced and define a channel 271 having an open proximal end and a distal end that is enclosed by a cross member 288. Each of the cam members 270a, 270b includes a first outer cam member 274 and a second inner cam member 276 which have cam surfaces as described above in regard to cam surfaces 174 and 176 and will not be described in further detail herein. The outer and inner cam members 274, 276 are laterally flexible and resilient. The inner cam member 276 includes a flexible portion 277 (FIG. 20) having an inwardly extending protrusion 277a that has a tapered distal surface.

Referring also to FIG. 21A-21C, the staple cartridge 206 defines a longitudinal axis, a central knife slot 240 extending along the longitudinal axis, and an outer and an inner cam slot 206a, 206b positioned on each side of the central knife slot 240. The outer cam slots 206a receive the outer cam members 274 of the actuation sled 220 and the inner cam slots 206b receive the inner cam members 276 of the actuation sled 220. The outer and inner cam members 274 and 276, respectively of the actuation sled 220 are laterally resilient and have proximal ends that, in an unbiased state, are angled outwardly in a direction away from the central knife slot 240 to a position misaligned with the longitudinal axis of the staple cartridge ("the misaligned position"). The outer and inner cam slots 206a, 206b define a proximal end 206c (FIG. 21 B) that is positioned distally of the proximal end of the staple cartridge 206. When the actuation sled 220 is in a fully retracted position, as described in further detail below, the inner and outer cam members 276 and 274 are positioned proximally beyond the proximal end 206c of the inner and outer cam slots 206b, 206a, such that the inner and outer cam members 276 and 274 are in the misaligned position (FIG. 21B). When the actuation sled 220 is advanced within the staple cartridge 206 from the fully retracted position, the inner and outer cam members 276, 274 move into the inner and outer cam slots 206b, 206a and are biased inwardly by walls defining the cam slots 206a, 206b to an aligned position in which the cam members 276, 274 are aligned with the longitudinal axis of the staple cartridge 206 (FIG. 23).

In the misaligned position of the inner and outer cam members 276, 274, the protrusions 277a on the flexible portion 277 of the actuation sled 220 are spaced from each other a distance to allow the base 242 of the clamp member 218 to pass between the protrusions 277a of the flexible portion 277 of the actuation sled 220 into the channel 271. In the aligned position of the inner and outer cam members 274, the protrusions 277a on the flexible portion 277 of the actuation sled 220 are spaced from each other a distance to prevent passage of the clamp member 218 proximally through the channel 271.

Referring briefly to FIG. 21A, the tool assembly 200 includes a support plate 214 that is similar to support plate 114 (FIG. 3) and includes a resilient protrusion, e.g., a resilient lance 214a (see also FIG. 4), that defines a stop surface for the actuation sled 220. When the actuation sled 218 is in its retracted position, the sled 218 is positioned atop the lance 214a to urge the lance 214a out of the path of the actuation sled 220. When the proximal end of the actuation sled 220 moves distally past the lance 214a, the lance 214a springs upwardly to a position to prevent proximal movement of the actuation sled 220 back to its retracted position.

Referring to FIGS. 21A-D, prior to actuating the tool assembly 200, the clamp member 218 and the actuation sled 220 are in a pre-clamped position. In the pre-clamped position, the clamp member 218 and the actuation sled 220 are in a nested relationship (FIG. 21D) in their retracted positions with the clamp member 218 located in a proximal portion of the channel 271 of the actuation sled 220 between the protrusions 277a on the flexible portions 277 of the actuation sled 220. In this position, the actuation sled 220 is positioned atop the lance 214a to bias the lance 214a out of the channel 271 of the actuation sled 220. In the pre-clamped position, substantially all of the length of the inner and outer cam members 276, 274 is positioned proximally of the proximal end 206c (FIG. 21B) of the inner and outer cam slots 206b, 206a.

Referring to FIGS. 22A-22C, when the drive screw 116 (FIG. 3) is actuated via the handle assembly 12 (FIG. 1) to advance the clamp member 218 through a clamping stroke, the clamp member 218 moves distally within the tool assembly 200 (FIG. 22A) independently of the actuation sled 220 in the direction indicated by arrow "F" in FIG. 22A from its retracted position (FIG. 21B) to the clamped position (FIG. 22B). As the clamp member 218 moves towards the clamped position through the channel 271 of the actuation sled 220, the upper beam 246 of the clamp member 218 engages the abutment surface 228 (FIG. 22A) of the anvil assembly 202 to pivot the anvil assembly 202 in the direction indicated by arrow "G" in FIG. 22A to the approximated position. Since the actuation sled 220 remains in an axially fixed position within the tool assembly, the actuation sled 220 remains positioned atop the lance 214a and the inner and outer cam members 276, 274 remain in the misaligned position located proximally of the proximal end 206c of the inner and outer cam slots 206b, 206a. In the clamped position of the clamp member 218, the clamp member 218 is positioned adjacent the cross-member 288 of the actuation sled 220.

In order to eject staples from the tool assembly 200, the drive member 116 (FIG. 3) is actuated again via the handle assembly 12 (FIG. 1) to move the clamp member 218 through a firing stroke. During the firing stroke, the clamp member 218 and the actuation sled 220 are moved through a first advancement stage shown in FIG. 23, through a retraction stage shown in FIGS. 24-25B, and through a second advancement stage shown in FIG. 26. Each of these stages is described below.

Referring to FIG. 23, during the first advancement stage of the firing stroke, the drive screw 116 (FIG. 3) advances the clamp member 218 in the direction indicated by arrows H. As the clamp member 218 moves distally through the tool assembly 200, the inner and outer cam members 276, 274 are advanced partially into the inner and outer cam slots 206b, 206a, respectively, such that the inner and outer cam members 276, 274 move to a position aligned with the longitudinal axis of the staple cartridge 206. After the first advancement stage of the firing stroke, the flexible portion 277 of the inner cam members 276 remains positioned proximally of the proximal end 206c of the outer cam slots 206a.

As the clamp member 218 moves distally within the tool assembly 200 during the first advancement stage of the firing stroke, the distal surface 242a of the clamp member 218 engages the cross member 288 of the actuation sled 220 to cause corresponding distal movement of the actuation sled 220 in the direction indicated by arrow "I". As the actuation sled 220 moves distally within the tool assembly 220, the actuation sled 220 moves off of the lance 214a (FIG. 22A) such that the lance 214a springs upwardly to a position proximally of the proximal end of the actuation sled 220.

Referring to FIG. 24-25B, during the retraction stage of the firing stroke, the drive screw 116 (FIG. 3) is rotated in an opposite direction to retract the clamp member 218 in the direction indicated by arrow "J" in FIG. 24 within the tool assembly 100. The lance 214a prevents proximal movement of the actuation sled 220 such that the clamp member 118 moves proximally within the channel 271 of the actuation sled 220 independently of the actuation sled 218. As the clamp member 218 moves proximally within the tool assembly 200, a proximal end of the base member 242 of the clamp member 218 engages a tapered distal surface of the inwardly extending protrusion 277a on the flexible portion 277 of the inner cam member 276 of the actuation sled 220. As discussed above, after the first advancement stage of the firing stroke, the flexible portion 277 of the inner cam member 276 is positioned proximally of the inner cam slot 206b. As such, when the base member 242 of the clamp member 218 engages the distal tapered surfaces of the protrusions 277a of the flexible portion 277, the flexible portion 277 of the inner cam member 276 flexes outwardly in the direction indicated by arrow "K" in FIG. 24 to allow the clamp member 218 to move proximally from within the channel 271 of the actuation sled 220 to a position proximally of the actuation sled 220 (FIGS. 25A-B). This movement allows the clamp member 218 to move proximally of the actuation sled 220 to position the knife 252 proximally of the inner and outer cam members 276, 274 such that during firing of the stapling device 10, stapling occurs before cutting of tissue.

Figure 26:
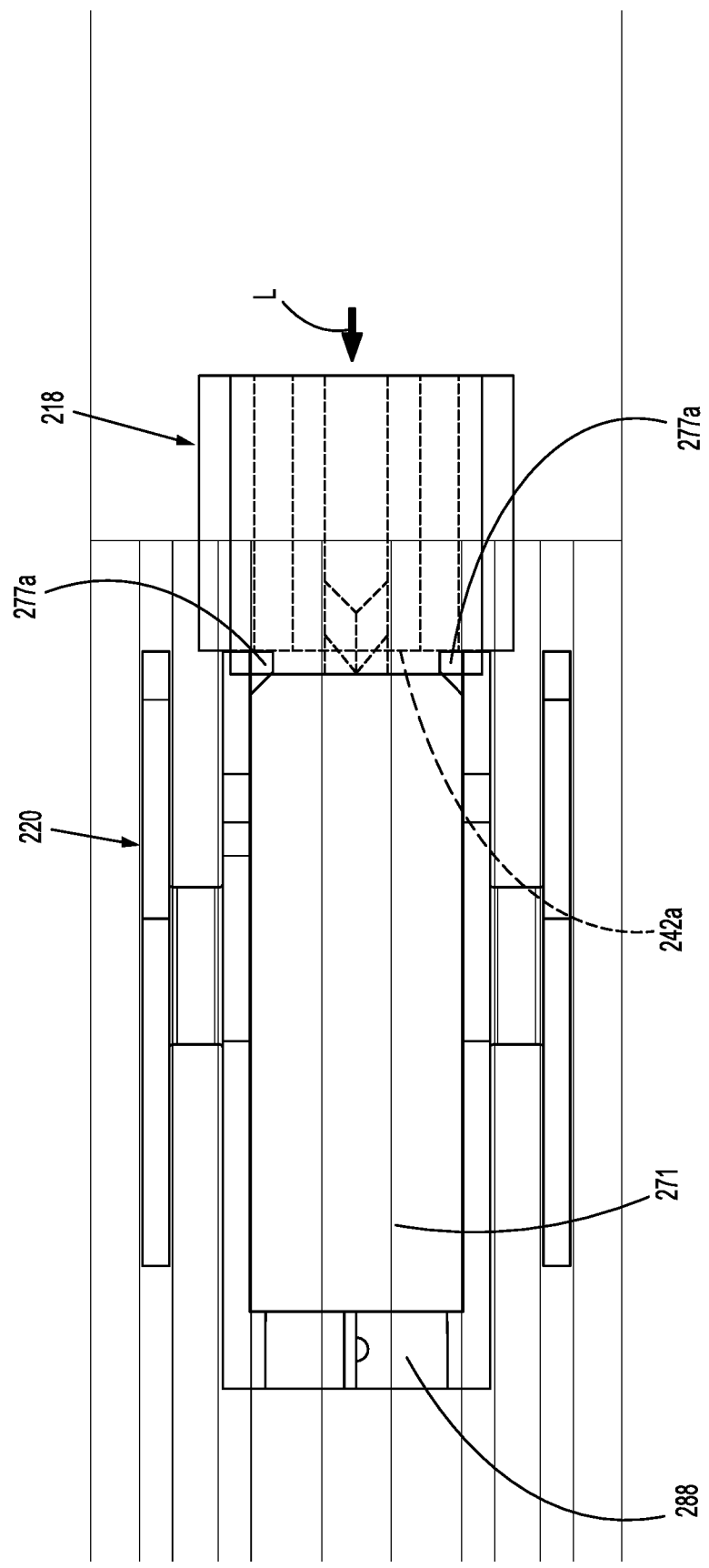
FIG. 26 is a top, schematic view of the tool assembly shown in FIG. 25A as the tool assembly is moved through a third stage of the firing stroke.

Referring to FIG. 26, during the second advancement stage of the firing stroke, the drive screw 116 (FIG. 3) is rotated to advance the clamp member 218 distally in the direction indicated by arrow "L" through the tool assembly 200 (FIG. 22A). Since the distal surface 242a of the clamp member 218 is positioned adjacent to the proximal side of the actuation sled 220 proximally of the protrusions 277a, distal movement of the clamp member 218 effects distal movement of the actuation sled 220 within the tool assembly 200. As the actuation sled 220 and the clamp member 218 are advanced through the tool assembly 200, the inner and outer cam members 276, 274 of the actuation sled 220 sequentially engage the pushers 110 (FIG. 3) to sequentially drive the staples 108 from the staple retention slots 124a and into tissue clamped between the cartridge and anvil assemblies.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A method of actuating a surgical stapling device including a tool assembly having an anvil and a cartridge assembly, the method comprising:
advancing a clamp member of the stapling device within the tool assembly independently of an actuation sled of the cartridge assembly to a clamped position to move the tool assembly from an open position to an approximated position;
advancing the clamp member through a firing stroke including moving the clamp member and the actuation sled distally through a first advancement stage, subsequently moving the clamp member proximally independently of the actuation sled through a retraction stage to position a knife of the clamp member proximally of cam surfaces of the actuation sled, and subsequently moving the clamp member and the actuation sled distally through a second advancement stage to eject staples from the cartridge assembly of the tool assembly.

2. The method of claim 1, wherein moving the clamp member and the actuation sled distally through the first advancement stage includes moving the actuation sled distally past a stop member positioned to prevent proximal movement of the actuation sled.

3. The method of claim 2, wherein moving the clamp member proximally independently of the actuation sled includes moving an engagement member of the clamp member to a position proximally of a cross-member formed on the actuation sled.

4. The method of claim 3, wherein moving the clamp member proximally independently of the actuation sled includes moving the engagement member under the cross-member as the actuation sled is engaged with the stop member.

5. The method of claim 1, further including positioning the clamp member within a channel defined by the actuation sled prior to advancing the clamp member to the clamped position.

6. The method of claim 5, wherein moving the clamp member proximally independently of the actuation sled occurs within the channel defined by the actuation sled.

7. The method of claim 1, further including using a drive screw to advance the clamp member to the clamped position and through the firing stroke.

8. The method of claim 3, wherein advancing the clamp member through the first and second advancement stages of the firing stroke includes advancing the engagement member into the cross-member of the actuation sled to advance the actuation sled.

9. The method of claim 1, wherein moving the clamp member proximally independently of the actuation sled through the retraction stage includes moving radial extensions of the clamp member within recesses defined by the actuation sled.

10. The method of claim 9, wherein moving the clamp member proximally independently of the actuation sled through the retraction stage further includes moving the radial extensions past a proximal end wall of the actuation sled that defines a proximal end of the recesses.

11. A method of actuating a surgical stapling device including a tool assembly having an anvil and a cartridge assembly, the method comprising:
advancing a clamp member of the stapling device and an actuation sled of the cartridge assembly through a firing stroke including advancing the clamp member and the actuation sled through a first advancement stage, subsequently moving the clamp member proximally independently of the actuation sled through a retraction stage to position a knife of the clamp member proximally of cam surfaces of the actuation sled, and subsequently moving the clamp member and the actuation sled distally through a second advancement stage to eject staples from the cartridge assembly of the tool assembly.

12. The method of claim 11, wherein moving the clamp member and the actuation sled distally through the first advancement stage includes moving the actuation sled distally past a stop member positioned to prevent proximal movement of the actuation sled.

13. The method of claim 12, wherein moving the clamp member proximally independently of the actuation sled includes moving an engagement member of the clamp member to a position proximally of a cross-member formed on the actuation sled.

14. The method of claim 13, wherein moving the clamp member proximally independently of the actuation sled includes moving the engagement member under the cross-member as the actuation sled is engaged with the stop member.

15. The method of claim 11, further including using a drive screw to advance the clamp member.

16. The method of claim 13, wherein advancing the clamp member through the first and second advancement stages of the firing stroke includes advancing the engagement member into the cross-member of the actuation sled to advance the actuation sled.

17. The method of claim 11, wherein moving the clamp member proximally independently of the actuation sled through the retraction stage includes moving radial extensions of the clamp member within recesses defined by the actuation sled.

18. The method of claim 17, wherein moving the clamp member proximally independently of the actuation sled through the retraction stage further includes moving the radial extensions past a proximal end wall of the actuation sled that defines a proximal end of the recesses.

\* \* \* \* \*